(12) United States Patent
Ihssen et al.

(10) Patent No.: US 10,287,330 B2
(45) Date of Patent: May 14, 2019

(54) METHODS AND COMPOSITIONS RELATING TO CRM197

(71) Applicant: GLAXOSMITHKLINE BIOLOGICAL S.A., Rixensart (BE)

(72) Inventors: Julian Ihssen, Gallen (CH); Michael Kowarik, Zurich (CH); Linda Christiane Thony-Meyer, Teufen (CH)

(73) Assignee: GLAXOSMITHKLINE BIOLOGICALS S.A. (BE)

( * ) Notice: Subject to any disclaimer, the term of this patent is extended or adjusted under 35 U.S.C. 154(b) by 0 days.

(21) Appl. No.: 14/655,801

(22) PCT Filed: Dec. 24, 2013

(86) PCT No.: PCT/EP2013/077968
§ 371 (c)(1),
(2) Date: Jun. 26, 2015

(87) PCT Pub. No.: WO2014/102265
PCT Pub. Date: Jul. 3, 2014

(65) Prior Publication Data
US 2015/0376245 A1    Dec. 31, 2015

Related U.S. Application Data

(60) Provisional application No. 61/746,366, filed on Dec. 27, 2012.

(51) Int. Cl.
*C07K 14/34* (2006.01)
(52) U.S. Cl.
CPC .................................. *C07K 14/34* (2013.01)
(58) Field of Classification Search
None
See application file for complete search history.

(56) References Cited

U.S. PATENT DOCUMENTS

| | | | |
|---|---|---|---|
| 4,356,170 | A | 10/1982 | Jennings et al. |
| 4,673,574 | A | 6/1987 | Anderson |
| 4,680,262 | A | 7/1987 | Bochner et al. |
| 4,709,107 | A | 11/1987 | West et al. |
| 5,601,827 | A | 2/1997 | Collier et al. |
| 5,846,711 | A | 12/1998 | Moore et al. |
| 5,917,017 | A | 6/1999 | Collier et al. |
| 6,455,673 | B1 | 9/2002 | Collier |
| 9,346,861 | B2 | 5/2016 | Dehottay et al. |
| 9,422,345 | B2 | 8/2016 | Blais et al. |
| 9,580,719 | B2 | 2/2017 | Retallack et al. |
| 9,994,622 | B2 | 6/2018 | Blais et al. |
| 2003/0157093 | A1 | 8/2003 | Neville, Jr. et al. |

FOREIGN PATENT DOCUMENTS

| | | |
|---|---|---|
| EP | 0208375 | 4/1989 |
| EP | 0161188 | 4/1991 |
| EP | D477508 A1 | 4/1992 |
| EP | 1762246 A1 | 3/2007 |
| WO | 9010015 | 9/1990 |
| WO | 1993015760 A1 | 8/1993 |
| WO | 1995008348 A1 | 3/1995 |
| WO | 1996029094 A1 | 9/1996 |
| WO | 1998042721 A1 | 10/1998 |
| WO | 0061762 A1 | 10/2000 |
| WO | 2005019466 A2 | 3/2005 |
| WO | 2005076010 A2 | 4/2006 |
| WO | 2010017383 A1 | 2/2010 |
| WO | 2010/150230 A1 | 12/2010 |
| WO | 2011/042516 A2 | 4/2011 |
| WO | 2011123139 A1 | 10/2011 |
| WO | 2011060431 A2 | 11/2011 |

OTHER PUBLICATIONS

Hiller et al., Nucleci Acids Res., 32, W375-379, 2004.*
Hengen , Trends in Biochem. Sci., 20 (7): 285-286, 1995.*
Dev et al., J. Bioenerg. And Biomemb., 22 (3): 271-289, 1989.*
Giannini et al., Nucl. Acids Res., vol. 12, No. 10, pp. 4063-4069, 1984 (Year: 1984).*
Stefan, et al., "Overexpression and purification of the recombinant diphtheria toxin variant CRM197" Journal of Biotechnology, Elsevier Science Publishers, J. Biotec., Aug. 15, 2011, vol. 156, No. 4, pp. 245-252.
Barbieri et al., Expression of a Mutant, Full-Length Form of Diphtheria Toxin in *Escherichia coli*, Infection & Immunity 55(7), 1647-51 (Jul. 1987).
Belyi et al., Construction of a fusion protein carrying antigenic determinants of enteric clostridial toxins, FEMS Microbiology Letters (2003)225(2):325-329.
Bethell, "A novel method of activation of cross-linked agaroses with 1,1-carbonyldiimidazole which gives a matrix for affinity chromatography devoid of additional charged groups."J. Biol. Chem.. 254:2572-4 (1979).
Biogegrain et al., Release of periplasmic proteins of Brucella suis upon acidic shock involves the outer membrane protein Omp25, Infection and Immunity 72(10) 5693-5703.
Bishai et al., "High level expression of a proteolytically sensitive diphtheria toxin fragment in *E. coli*"J. Bacteriol., 169:5140-5151 (1987).
Chaussee et al., Streptococcal erythrogenic toxin B abrogates fibronectin-dependent internalization of S. pyogenes by cultured mammalian cells. Infection and Immunity (2000) 68(6):3226-32.
Chen et al., "A modified osmotic shock for periplasmic release of a recombinant creatinase from *E coli*" Biochem Eng J. 19:211-215 (2004).
Chu et al., "Further studies on the immunogenicity of haemophilus influenzae Type b and pneumococcal type 6A polysaccharide-protein conjugates"Infection Immunology 40(1):245-256 (1983).

(Continued)

*Primary Examiner* — Nancy A Treptow

(57) ABSTRACT

The present invention provides novel methods of producing diphtheria toxin. In particular, the present invention provides novel methods of producing nontoxic forms of diphtheria toxin, e.g., CRM197. The present invention also provides novel compositions comprising diphtheria toxin or nontoxic forms of diphtheria toxin, e.g., CRM197.

27 Claims, 3 Drawing Sheets

Figure 1:
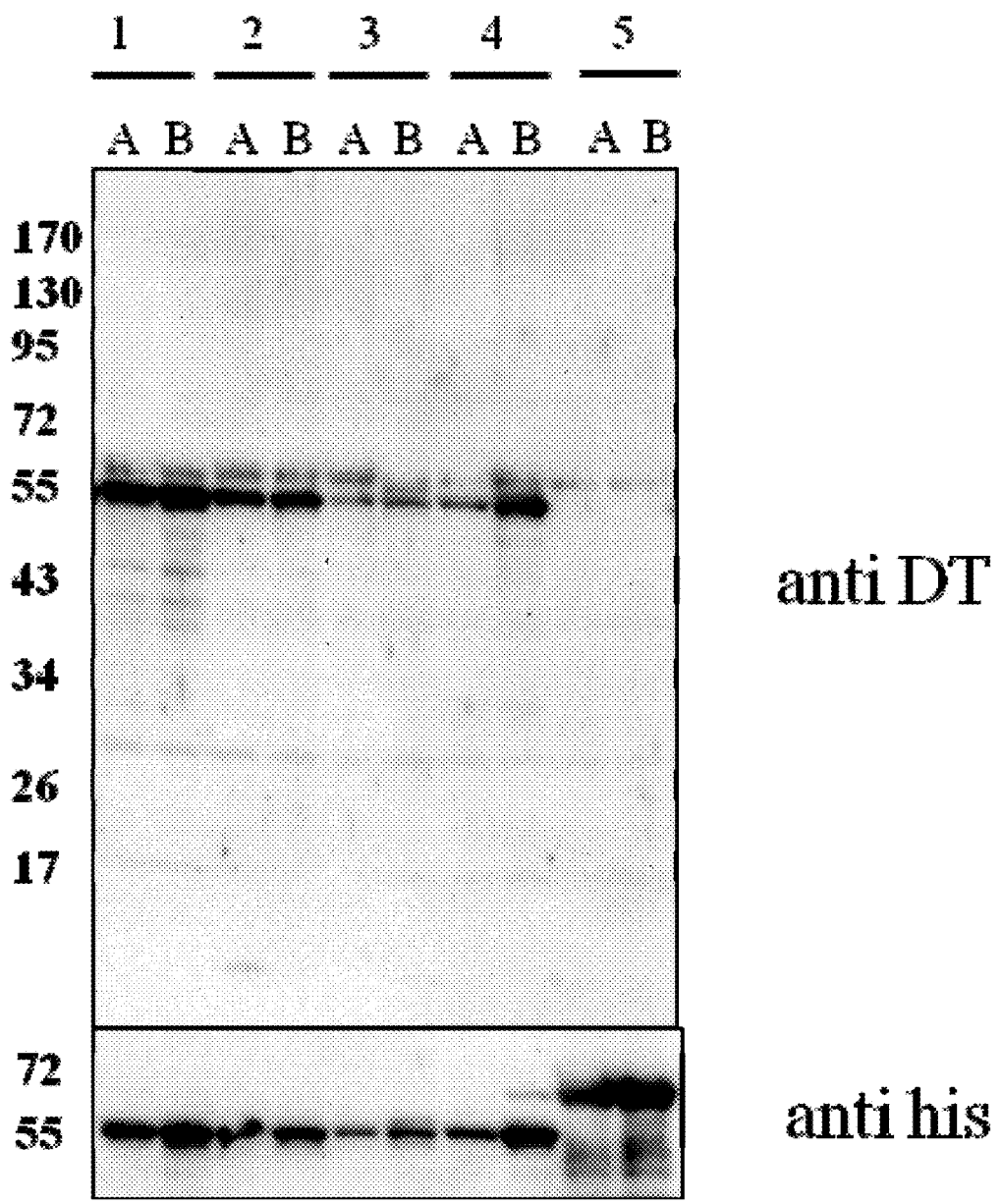

Specification includes a Sequence Listing.

(56) References Cited

OTHER PUBLICATIONS

Competty, B.: "Production of Human Paraoxonase I (huPONI) in *E coli* with Periplasmic Expression and Chaperone Co-expression. Senior Honors Thesis. The Ohio State University", Mar. 2009 (2009-03), pages 1-35.

Hearn et al., "Application of 1,1 carbonyldiimidazole-activated matrices for the purification of proteins" J. Chromatography 218:509-518 (1981).

Huber et al., Use of thioredoxin as a reporter to identify a subset of E coli signal sequences that promote signal recognition particle-dependent translocation. J. Bacteriol 187(9), 2983-91 (2005).

Humphreys et al., High-level periplasmic expression in *e.coli* using a eukaryotic signal peptide: importance of codon usage at the 5'end of the coding sequence. Protein Expression and Purification 20:252 (2000).

Kaczorek et al., Nucleotide Sequence and Expression of the Diphtheria tox228 Gene in *Escherichia coli*, Science 221, 855-58 (1983).

Lei et al., Characterization of the Erwinia carotovora pelB Gene and Its Product Pectate Lyase, J. Bacteriol. 169(9), 4379-83 (Sept 1987).

Leong et al., Cloned Diphtheria Toxin Fragment A Is Expressed from the tox Promoter and Exported to the Periplasm by the SecA Apparatus of *Escherichia coli*K1, J. Biological Chem. 258(24), 15016-20 (Dec. 25, 1983).
Mekada et al., Binding properties of diphtheria toxin to cells are altered by mutation in the fragment a domain. J. Biol. 2,hem_ 260(22) (1985).
O'Keefe et al., Cloned diptheria toxin within the periplasm of *Escherichia coli*causes lethal membrane damage at low pH, PNAS 86(1):343-346 (1989).
Oh et al., Translocation of the catalytic domain of diphtheria toxin across planar phospholipid bilayers by its own T domain. PNAS USA 96 (1999).
Paoletti et al., Preclinical Evaluation of Group B Streptococcal Polysaccharide Conjugate Vaccines Prepared with a Modified Diphtheria Toxin and a Recombinant Duck Hepatitis B Core Antigen, Vaccine 20, 370-76 (2002).
Rairakhwada, et al., "Gene cloning, characterization, and heterologous expression of levansucrase from Bacillus amyloliquefaciens"J. Ind. Microbiol. Biotechol. 37:195-204 (2010).
Rathore et al., Optimization of osmotic shock procedure for isolation of a protein product expressed in *E coil*, Biotechnology Progress, 19(5):1541-1546 (2003).
Retallack et al., Transport of Heterologous Proteins to the Periplasmic Space of Pseudomonas fluorescens Using a Variety of Native Signal Sequences, Biotechnol. Lett. 29, 1483-91 (2007).
Sletta et al., Broad-Host-Range Plasmid pJB658 Can Be Used for Industrial-Level Production of a Secreted Host-Toxic Single-Chain Antibody Fragment in *Escherichia coli*, Applied & Environmental Microbiol. 70(12), 7033-39 (Dec. 2004).
Sletta et al., The Presence of N-Terminal Secretion Signal Sequences Leads to Strong Stimulation of the Total Expression Levels of Three Tested Medically Important Proteins During High-Cell-Density Cultivations of *Escherichia coli* , Applied & Environmental Microbiology 73(3), 906-12 (Feb. 2007).
Sudhir Sandev et al "Production of active eukaryotic proteins through bacterial expression systems: A review of the existing biotechnology", Molecular and Cellular Biochemistry, vol. 307: 249-264, Feb. 2008.
Tan et al., *E. coil*Selection of Human Genes Encoding Secreted and Membrane Proteins Based on cDNA Fusions to a Leaderless β-Lactamase Reporter, Genome Research 13, 1938-43 (Cold Spring Harbor Lab. Press, 2003).
Terpe, Overview of Bacterial Expression Systems for Heterologous Protein Production: From Molecular and Biochemical Fundamentals to Commercial Systems, Appl. Microbiol. Biotechnol. 72, 211-22 (2006).
Titball et al, Molecular Cloning and nucleotide sequence of the alpha-toxin (phospholipase C) of Clostridium perfringens, Infection and Immunity 57(2):367 - 376 (1989).
Yamamoto et al., High level expression of *Streptococcus pyogenes*erhthrogenic toxin a (SPE S) in *E. coli* and its rapid purification by HPLC, FEMS Microbiol Letters (1995) 132(3):209-213.
Zabriskie et al., "Effects of fermentation feeding strategies prior to induction of expression of a recombinant malaria antigen in *E coli*"J. Ind. Microbiol. 2:87-95 (1987).
Leong et al., Cloned Diphtheria Toxin Fragment A Is Expressed from the tox Promoter and Exported to the Periplasm by the SecA Apparatus of *Escherichia coil*K1, J. Biological Chem. 258(24), 15016-20 (Dec. 25, 1983).

* cited by examiner

METHODS AND COMPOSITIONS RELATING TO CRM197

CROSS-REFERENCE TO RELATED APPLICATIONS

This application is filed pursuant to 35 U.S.C. § 371 as a United States National Phase Application of International Application No. PCT/EP2013/077968 filed 24 Dec. 2013, which claims priority to U.S. Provisional Ser. No. 61/746,366 filed 27 Dec. 2012.

REFERENCE TO SEQUENCE LISTING SUBMITTED ELECTRONICALLY VIA EFS-WEB

The content of the electronically submitted sequence listing on ASCII text file (Name: LB65508US Sub Seq Lstg ST25; 45,456 bytes; and Date of Creation: Mar. 7, 2017) is incorporated herein by reference in its entirety.

1 INTRODUCTION

The present invention provides novel methods of producing diphtheria toxin. In particular, the present invention provides novel methods of producing nontoxic forms of diphtheria toxin, e.g., CRM197. The present invention also provides novel compositions comprising diphtheria toxin or nontoxic forms of diphtheria toxin, e.g., CRM197.

2 BACKGROUND

The CRM197 protein is a safe and effective T-cell dependent carrier for saccharides and is currently being used in many different vaccine formulations called conjugate vaccines. Diphtheria toxin is a protein exotoxin produced by the bacterium *Corynebacterium diphtheriae* upon infection with the phage 0197. Both, Diphtheria toxin ("DT") and CRM197 are components of many vaccines, like for example against *Bordatella pertussis, Clostridium tetani, C. diphtheriae*, hepatitis B virus, and *Haemophilus influenza* type B (WO 9324148, WO 9700697, WO 02055105). In addition there has been a growing interest in CRM197 because of its potential antitumor activity relating to its capacity to bind the soluble form of HB-EGF (US 2006/0270600A1).

CRM197 is produced by *C. diphtheriae* infected by the non-toxigenic phage β197tox. β197tox was created by nitrosoguanidine mutagenesis of the toxigenic corynephage β (Uchida, T. et al. 1971, Nature New Biology 233:8-11). The CRM197 protein is a nontoxic form of diphtheria toxin but is immunologically indistinguishable from the diphtheria toxin. DT has a mass of 58.350 kDa (CRM197=58.415 kDa) and consists of the N-terminal A and the C-terminal B domains (21 and 37 kDa) which are linked by a disulfide bridge connecting Cys186 and Cys201. The A fragment is toxic after being released from its disulfide-bonded partner, the B fragment. Nicking of the holotoxin by mild proteolysis at the connecting peptide at positions 191-3 is a prerequisite for the A fragment activation. The B fragment has no apparent enzymatic activity but is required for toxicity, probably due to targeting the holotoxin to the target cell membranes (Broker M, Costantino P, De Tora L, McIntosh E D, Rappuoli R: Biochemical and biological characteristics of cross-reacting material 197 (CRM197), a non-toxic mutant of diphtheria toxin: use as a conjugation protein in vaccines and other potential clinical applications. *Biologicals,* 2011, 39(4):195-204.)

Infected *C. diphtheriae* cultures secrete the CRM197 protein across the cytoplasmic membrane out of the cell into the culture medium. The CRM197 protein has about the same molecular weight as the diphtheria toxin but differs therefrom by a single base change (guanine to adenine) in the structural gene. This single base change causes an amino acid substitution (glutamic acid for glycine, G52E) in the mature protein and eliminates the toxic properties of diphtheria toxin (Giannini G, Rappuoli R, Ratti G: The amino-acid sequence of two non-toxic mutants of diphtheria toxin: CRM45 and CRM197. *Nucleic Acids Res* 1984, 12(10): 4063-4069).

Methods of preparing DT and CRM197 are described in U.S. Pat. No. 4,709,017, U.S. Pat. No. 5,843,711, U.S. Pat. No. 5,601,827, and U.S. Pat. No. 5,917,017. There are currently three different systems used for industrial preparation of CRM197. Two systems are based on the use of phage infected *C. diphtheriae* cells. The most recent development constitutes a recombinant expression system in *Pseudomonas fluorescens*. The method employs a secretion approach to the periplasm in a genetically optimized *P. fluorescens* strain using a CRM197 gene equipped with a signal peptide for secretion into the periplasm (US20110287443).

For example, diphtheria toxin is isolated from cultures of *C. diphtheriae* strain C7 (B197) and/or *C. diphtheriae* strain C7 (B197) pPx350 grown in a casamino acids and yeast extract-based medium under aerobic conditions. Adjustment of media components were shown to improve yields (U.S. Pat. No. 4,925,792, WO 2006 100108). CRM197 or DT are harvested from the supernatant of the culture, and concentrated by ultrafiltration. Ammonium sulfate precipitation is a first, and anionic exchange chromatography a second purification step.

However, production of significant quantities of the CRM197 protein for use in vaccines has been hindered due to low protein abundance (WO 2006 100108).

Techniques have been developed to bolster the production of CRM proteins using double lysogens (Isolation and characterization of *C. diphtheriae* nontandem double lysogens hyperproducing CRM197. R Rappuoli, *Appl. Environ, Microbiol.* September 1983 46:560-564; U.S. Pat. No. 4,925,792 issued to R. Rappuoli; and Integration of corynebacteriophages beta tox+, omega tox+, and gamma tox- into two attachment sites on the *C. diphtheriae* chromosome. R Rappuoli, J L Michel, and JR Murphy; *J. Bacteriol. March* 1983 153:1202-4210) of the nontoxigenic corynephage β197. Rappuoli reports yields of CRM197 from double and triple lysogens up to three fold higher than from the single lysogens. The production levels of CRM197 by single lysogens are adequate but economically unsatisfactory for the production of vaccines which utilize CRM197 protein. It is important to note that the construction of double and triple lysogenic strains in order to increase expression efficiency in *C. diphtheria e* is a long process which requires a laborious screening phase.

Plasmids were developed for recombinant expression of CRM197 in *C. diphtheriae* (U.S. Pat. No. 5,614,382, 1995/5614382_1997). This makes it possible to increase the number of copies of the gene (up to 5-10 per cell) without having to select pluri-lysogenic bacterial strains.

As in the case of the *Corynebacterium* strains infected by the phage β197tox, CRM197 is expressed in special culture media with a low ferrous content. Despite a reduction in the amount of time required for the genetic handling of the bacterial strain, the output of CRM197 does not increase dramatically by comparison with the use of double lysogenes.

Alternative expression host cells for DT included a *Salmonella typhi* vaccine strain cvd 908-htra (Orr N, Galen J E, Levine M M: Expression and immunogenicity of a mutant diphtheria toxin molecule, CRM197, and its fragments in *S. typhi* vaccine strain CVD 908-htrA. *Infect Immun* 1999, 67(8):4290-4294). *Salmonella* is a Gram negative bacterium and similar expression host as *E. coli*. Expression levels from various constructs (with, without signal peptide) in cvd 908-htra were low and solubility and immunogenicity were poor. Utilizing the alternative, non-Sec dependent translocation system of the hemolysin operon improved expression of soluble DT, but levels were still low.

Reports for production of CRM197 in *E. coli* show low yields of soluble CRM197 and formation of insoluble product in inclusion bodies. Truncation approaches have been used in an attempt to enhance expression to higher levels. (Bishai W R, Miyanohara A, Murphy J R: Cloning and expression in *E. coli* of three fragments of diphtheria toxin truncated within fragment B. *Journal of Bacteriology* 1987, 169(4):1554-1563)

A single strand expression plasmid for CRM197 containing the mutated diphtheria toxin gene encoding CRM197 was used for expression in *E. coli* (Bishai W R, Rappuoli R, Murphy J R: High-level expression of a proteolytically sensitive diphtheria toxin fragment in *Escherichia coli*. *Journal of Bacteriology* 1987, 169(11):5140-5151; Bishai 1987). In this publication, transcription of CRM197 was controlled by the endogenous and constitutive Ptox promotor. In addition, DT C-terminally fused to the alpha melanocyte stimulating hormone ("ABM508") was expressed by the heat inducible $P_{Lambda}$ promoter or the $P_{tac}$ promoter for expression.

Bishai 1987 speculated that jamming of the secretion apparatus due to high level protein induction caused a growth stop after induction of expression of periplasmic DT/CRM197 variants. This can be a general problem in periplasmic protein expression that has been observed and resulted in low volumetric yields of protein previously (Benson S A, Hall M N, Silhavy T J: Genetic analysis of protein export in *E. coli* K12. *Annual Review of Biochemistry* 1985, 54:101-134). Jamming of the secretion apparatus and formation of insoluble protein suggested an inability of the *E. coli* cells to provide a productive translocation and folding environment for CRM197 biogenesis.

As a consequence, Bishai 1987 reasoned that cytoplasmic expression would avoid the translocon jamming. Thus, Bishai 1987 removed the signal peptide for directing the expression into the cytoplasm. Only at low temperatures and when cytoplasmic proteases were deleted, did the cytoplasmic expression constructs yield soluble product. Production was inefficient and lead to aggregates at elevated temperatures, and when proteases were present.

Bishai 1987 failed to show production of high levels of soluble protein CRM197 fusion protein, i.e., with signal peptide for periplasmic targeting. In a Coomassie stained SDS polyacrylamide gel, extracts containing the ABM508 expression construct showed an intense protein band corresponding to ABM508, whereas cells expressing CRM197 expressed from the natural promoter with the wild type signal peptide do not show an obvious band for CRM197 at the expected size of 58 kDa.

Thus, periplasmic expression was not considered an efficient production strategy and to date there is no efficient *E. coli* periplasmic expression system established for production of soluble and correctly folded CRM197 or DT.

A production system which is based on the cytoplasmic expression of insoluble CRM197 in inclusion bodies followed by solubilization, purification and refolding of the protein is provided by the first *E. coli* based expression system for CRM197 (WO2010 150230). Wild-type CRM197 without additional amino acids can only be obtained with this system when an additional proteolysis step is applied.

Signal peptides induce protein secretion to the periplasm and have various effects on protein biogenesis. (Powers T, Walter P: Co-translational protein targeting catalyzed by the *E. coli* signal recognition particle and its receptor. *The EMBO Journal* 1997, 16(16):4880-4886.) (Schierle C F, Berkmen M, Huber D, Kumamoto C, Boyd D, Beckwith J: The DsbA signal sequence directs efficient, cotranslational export of passenger proteins to the *E. coli* periplasm via the signal recognition particle pathway. *Journal of Bacteriology* 2003, 185(19):5706-5713).

3 SUMMARY

Provided herein is a method to produce soluble, folded, full length CRM197 at high yields (e.g., at least 0.5 mg/1) in *E. coli* expression strains. In particular, a signal peptide is used to direct secretion of the protein into the periplasmic space.

Provided herein are methods for producing CRM197 wherein the method comprises culturing an *E. coli* cell comprising a nucleic acid encoding CRM197 wherein CRM197 is fused to a heterologous signal peptide that targets CRM197 to the periplasm of the *E. coli* cell. In more specific embodiments, the wild type signal peptide of CRM197 has been deleted. In even more specific embodiments, the wild type signal peptide of CRM197 has been replaced by the heterologous signal peptide. The heterologous signal peptide can be selected from the group consisting of the signal peptide from *E. coli* heat-labile enterotoxin, *E. coli* outer membrane porin (OmpA), *E. coli* maltose binding protein (MalE), *E. carotovorans* pectate lyase (PelB), and *Bacillus* sp. endoxylanase (XynA). CRM197 can be produced at a concentration of at least 5, 10, 25, 50, 75, 100, 125, 125, 150, 175, 200, 225, 250, 300, 400, 500, 600, 700, 800, 900, or at least 1000 mg protein per liter culture medium. At least 50% of the produced protein is properly folded as determined by circular dichroism. At least 10%, 20%, 30%, 40%, 50%, 60%, 70%, 80%, 90%, 95%, 98%, 99%, 99.5%, 99.8%, or at least 99.9% of the produced protein is properly folded. At least 50% of the produced protein is not present in aggregates. At least 10%, 20%, 30%, 40%, 50%, 60%, 70%, 80%, 90%, 95%, 98%, 99%, 99.5%, 99.8%, or at least 99.9% of the produced protein is not present in aggregates. At least 50% of the produced protein is soluble. At least 10%, 20%, 30%, 40%, 50%, 60%, 70%, 80%, 90%, 95%, 98%, 99%, 99.5%, 99.8%, or at least 99.9% of the produced protein is soluble.

In certain embodiments, the heterologous nucleotide sequence encodes a cleavage site between the signal peptide that targets CRM197 to the periplasm and the CRM197 protein wherein the cleavage site comprises the amino acid sequence aa1-aa2-aa3-(cleavage site)-aa4-aa5-aa6-aa7-aa8, wherein aa1 is selected from Ala, Ser, Gly, Cys, Thr, and Gln;

aa2 is selected from any natural amino acid;

aa3 is selected from any natural amino acid except Phe, His, Tyr, Trp, Asp, Glu, Lys, Arg Asn, and Gln;

aa4 to 8 is selected from ala-asp-asp-val and gly-ala-asp-asp and met-gly-ala-asp;
or wherein the cleavage site comprises the amino acid sequence aa1-aa2-aa3-(cleavage site)-aa4-aa5-aa6-aa7-aa8, wherein aa4 to 8 is selected from ala-asp-asp-val and gly-ala-asp-asp and met-gly-ala-asp; and wherein the first 70 aa of the open reading frame results in a Y score when analyzed by SignalP 4.0 Server of more than 0.72.

In certain specific embodiments, the heterologous nucleotide sequence encodes the protein of SEQ ID NO: 1 or 2. The heterologous nucleotide sequence can be operatively linked to a promoter selected from the group consisting of the 1-arabinose inducible araBAD promoter (PBAD), the lac promoter, the 1-rhamnose inducible rhaP BAD promoter, the T7 RNA polymerase promoter, the trc and tac promoter, the lambda phage promoter p L, and the anhydrotetracycline-inducible tetA promoter/operator.

In certain embodiments, the nucleic acid encoding CRM197 is inserted in a high copy expression plasmid. The high copy expression plasmid can be pEC415, pBR322, pBAD, pET series, pUC series, pACT3, pEXT22, pEXT20, pBLUESCRIPT series, pGEM series.

In certain embodiments, the expression of CRM197 can be induced at a culture density of OD600>0.3. Specifically, the expression of CRM197 can be induced at a culture density of OD600>0.5, >1, or >1.5.

CRM197 can be expressed at a temperature of 37° C. CRM197 can be expressed at a temperature of 20, 25, 30, 32, or 35° C.

In certain embodiments, at least 50% of CRM197 protein that has been produced in accordance with the methods provided herein have an N-terminus of ADDV (SEQ ID NO: 7), GADDV (SEQ ID NO: 9), or MGADDV (SEQ ID NO: 12). More specifically, at least 60%, 70%, 80%, 90%, 95%, 98%, 99%, at least 99.5% or 100% of the expressed CRM197 have an N-terminus of ADDV (SEQ ID NO: 7), GADDV (SEQ ID NO: 9), or MGADDV (SEQ ID NO: 12). In certain embodiments, at least 50% of the expressed CRM197 have a disulfide bond between Cys186 and Cys201. At least 60%, 70%, 80%, 90%, 95%, 98%, 99%, at least 99.5% or 100% of the expressed CRM197 have a disulfide bond between Cys186 and Cys201.

3.1 Terminology

DT-Diphtheria Toxin

CRM197-Cross reactive material 197, DT with a mutation of glycine 52 to glutamate, G52E AMB508-fusion protein consisting of alpha melanocyte-stimulating hormone sequence fused to the CRM197 sequence β197tox-non-toxigenic corynephage 197 preprotein-protein including the signal peptide mature protein, processed protein-protein after signal peptide cleavage IPTG-Isopropyl-β-D-thiogalactopyranosid, inducer for lac, trc, and related promoters, to be added to the growth media at induction time ParaBAD-promoter of the araBAD operon, inducible by the addition of L-arabinose to the growth media

4 BRIEF DESCRIPTION OF THE DRAWINGS

FIG. 1 Expression of CRM197 in *E. coli*. Different expression plasmids (1, 2, 3, 4, 5 indicating p932, p934, p722, a cytoplasmic CRM197 variant, and p150 (see, Table 2)) were tested for CRM197 expression in *E. coli* BL21 cells (lanes indicated by A) or W3110 (B). Total cell extracts normalized to OD600 after 2 hours of induction were prepared and analyzed. The top panel shows a Western blot using anti DT antiserum, bottom panel was detected using anti his tag antiserum.

FIG. 2. Purification of soluble CRM197 from *E. coli*. Two different strains containing expression plasmids (1, 2, indicating p932, p933) in BL21 were grown as described in the text. Elution fractions were separated by SDS PAGE and stained by Coomassie blue (left panel) and immunodetected after electrotransfer to nitrocellulose membranes using anti DT antiserum.

FIG. 3. Periplasmic expression levels of CRM197 fused to different N-terminal signal peptides in comparison to a well-secreted reference protein EPA-6H, recombinant, genetically detoxified *Pseudomonas aeruginosa* exotoxin A (EPA), (Ihssen J, Kowarik M, Dilettoso S, Tanner C, Wacker M, Thony-Meyer L: Production of glycoprotein vaccines in *E. coli*. Microbial cell factories 2010, 9:61). Coomassie stained SDS-PAGE gel with periplasmic extracts of *E. coli* strains harboring plasmids 1 to 16 as described in Table 2. Cells were grown in shake flasks at the optimal expression temperature in TB medium and induced at an $OD_{600}$ of 0.4-0.6 by the addition of 4 g/1 L-arabinose. OD equivalent samples for extraction of soluble periplasmic proteins (sucrose-lysozyme method) were taken 4 h after induction, with the exception of 13*: sample taken before induction. M: protein marker mix, Thermo-Scientific prestained protein ladder #26616, 3 μL (concentration of individual proteins 0.1-0.2 mg/ml).

5 DETAILED DESCRIPTION

Provided herein are methods for the expression of diphtheria toxin and nontoxic forms of diphtheria toxin, e.g., CRM197. More specifically, provided herein are methods for the expression of CRM197 and secretion of CRM197 into the periplasmic space of *E. coli* cells in a soluble and correctly folded form.

In certain embodiments, CRM197 is expressed using a heterologous signal peptide that targets CRM197 in the periplasmic space of the host cell. In certain more specific embodiments, the host cell is *E. coli*. An expression cassette containing the CRM197 gene and a heterologous signal peptide can be constructed using standard molecular biology techniques. Specifically, the wild type signal peptide of CRM197 is deleted and a heterologous signal peptide is introduced instead. On a nucleic acid level, care should be taken that the sequence encoding the signal peptide is cloned in frame with the nucleic acid encoding the remainder of CRM197. In certain specific embodiments, the heterologous signal peptide replaces the wild type signal peptide. In other embodiments, the wild type signal peptide is deleted or functionally inactivated and the heterologous signal peptide is introduced at a different location of the protein. In certain embodiments, a proteolytic cleavage site is introduced between the signal peptide and the remainder of the molecule. The proteolytic cleavage site can be recognized and cleaved in the periplasm of the host cell. In certain more specific embodiments, the signal peptidase is recombinantly expressed in the host cell.

In certain embodiments, the following parameters can affect the expression of the protein of interest. More detailed information on these various aspects are provided in the following sections.

The nucleic acid can encode the mature, secreted CRM197 (SEQ ID NO:6):

i) in a fashion optimized for *E. coli* codon usage.
ii) A heterologous signal sequence can be used for targeting CRM197 to the periplasmic space in *E. coli*. By standard cloning procedures, synthetic DNA sequences encoding a heterologous signal peptide can be fused at the N-terminus of the mature CRM197 gene. Different N-terminal signal peptides such as from *E. coli* heat-labile enterotoxin, *E. coli* outer membrane porin A (OmpA), *E. coli* maltose binding protein (MalE), *E. coli* DsbA, *Erwinia carotovorans* pectate lyase (PelB), or *Bacillus* sp. endoxylanase (XynA), can be used with the methods provided herein. In certain embodiments, a particular heterologous signal peptide has been demonstrated to confer secretion of recombinant proteins into the periplasmic space of *E. coli.*
iii) The signal peptide cleavage site (i.e. the sequence between the signal peptide and the secreted protein); For example, signal peptide cleavage prediction programs, such as for example SignalP 4.0 server program (hosted at the website of the Center for Biological Sequence Analysis of the Technical University of Denmark), can be used to design alternative signal peptide cleavage sites. This program predicts i) cleavage site probability, and ii) cleavage site location, i.e. between which amino acids cleavage is most likely to occur. In specific embodiments, signal peptide cleavage sites are designed in a way to result in a CRM197 N terminus as similar as possible to the natural N-terminus.
iv) A suitable high copy number expression plasmid can be used with the methods provided herein.
v) Expression of CRM197 can be positioned under the control of the high level induction arabinose promoter.
vi) The growth medium;
vii) The expression time, i.e. the point of induction during growth and the time between induction and harvest of the cells;
viii) Amount of inducer;
ix) The expression temperature;

In general, a method provided herein is conducted as follows. First, an expression plasmid as described herein is introduced into a host cell (e.g., *E. coli* or *Salmonella* sp expression strain). The transformation mix can be plated on rich media supplemented with the antibiotic for which the expression plasmid carries a resistance marker. A single colony can be used to inoculate a small culture volume (e.g., 5 ml) consisting of, e.g., TB medium, or a similar rich medium containing glycerol as a carbon source and lacking or supplemented with the suitable antibiotic. The culture can then be incubated between 20-35° C. until stationary phase and then diluted to fresh medium of identical or similar composition, pre-warmed at 20-35° C., at a ratio of 1:50 to 1:100. The fresh culture can then be grown to exponential growth phase ($OD_{600}$ of 0.6-1.2) and expression is induced by the addition of the appropriate inducer, which depends on the promoter used in the expression plasmid. Examples of inducers include arabinose or a different chemical of physical condition for high level protein induction. Then, expression is continued. In certain embodiments, expression is continued before harvesting for at least 2, 4, 6, 8, 10, 12, 14, 16, 18, 20, 22, 24, 26, 28, or at least 30 hours.

Samples can be taken at any time. At all-time points the amount of soluble CRM197 formed is evaluated by analysis via SDS-PAGE and Coomassie staining of periplasmic extracts. A comparison to commercial CRM197 of known concentration allows estimating the yield.

In certain embodiments, the following control is used to determine that the expressed CRM197 protein is soluble. Without being bound by theory, such soluble protein is correctly folded. CRM197 detected at around 58 kDa in periplasmic extracts prepared by the sucrose-lysozyme method (Kowarik M, Young N M, Numao S, Schulz B L, Hug I, Callewaert N, Mills D C, Watson D C, Hernandez M, Kelly J F et al: Definition of the bacterial N-glycosylation site consensus sequence. The EMBO journal 2006, 25(9): 1957-1966) can be used as a standard for soluble protein.

In certain embodiments, provided herein are methods that result in a concentration of properly folded CRM197 of at least 1 mg/l, 2 mg/l, 3 mg/l, 4 mg/l, 5 mg/l, 6 mg/l, 7 mg/l, 8 mg/l, 9 mg/l, 10 mg/l, 11 mg/l, 12 mg/l, 13 mg/l, 14 mg/l, 15 mg/l, 20 mg/l, 25 mg/l, 50 mg/l, 75 mg/l, or at least 100 mg/l.

In certain embodiments, depending on the signal peptide cleavage site sequence, the N terminus of CRM197 can be ADDV (SEQ ID NO: 7), or GADDV (SEQ ID NO: 9), or MGADDV (SEQ ID NO: 12).

In certain embodiments, at least 50%, 60%, 70%, 75%, 80%, 85%, 90%, 95%, 98%, 99%, or 100% of the resulting CRM197 proteins have a disulfide bond between Cys186 and Cys201 connecting A and B fragments. The presence of this disulfide bond can be demonstrated using a thiol assay (Hansen R E, Ostergaard H, Norgaard P, Winther J R: Quantification of protein thiols and dithiols in the picomolar range using sodium borohydride and 4,4'-dithiodipyridine. Anal Biochem 2007, 363(1):77-82).

In certain embodiments, at least 50%, 60%, 70%, 75%, 80%, 85%, 90%, 95%, 98%, 99%, or 100% of the resulting CRM197 proteins are soluble and are not present in aggregates.

5.1 Proteins of Interest

The present invention describes production methods for DT and CRM197. Illustrative protein sequences for CRM197 are provided as SEQ ID NOs: 3 and 4, and the corresponding full length expression plasmid DNA sequences are SEQ ID NOs: 1 and 2.

5.2 Periplasmic Targeting

Various secretory pathways from the cytoplasm to the periplasm exist in *E. coli*. These pathways include the Sec pathway, the SRP dependent pathway, and the twin arginine pathway for secretion. The TatABC pore is thought to be responsible for the secretion of folded proteins. Without being bound by theory, the signal peptide can determine which secretory pathway is chosen by the cell. (Driessen A J, Nouwen N: Protein translocation across the bacterial cytoplasmic membrane. Annual review of biochemistry 2008, 77:643-667.)

In certain embodiments, the heterologous signal peptide for use with the present methods is an amino-terminal hydrophobic signal sequences that is cleaved during the translocation process. In certain embodiments, conditions for a method provided herein are chosen such that the protein does not fold into its stable three-dimensional structure in the cytoplasm of the host cell. Without being bound by theory, folding in the cytoplasm may prevent export. In certain other embodiments, the heterologous signal peptide encodes an arginine signature that targets the protein to the twin arginine pathway for secretion.

In certain embodiments, an unfolded protein may be maintained in an export competent state in several different ways: (i) the heterologous signal peptide can be chosen such that the protein may be translocated across a membrane simultaneously with translation of the protein, thus ensuring that not even its secondary structures are formed in the cytoplasm due to the absence of amino acid polymer; (ii) chaperones or antifolding factors that prevent folding in the cytoplasm (Randall L L, Topping T B, Smith V F, Diamond D L, Hardy S J: SecB: a chaperone from *E. coli*. Methods Enzymol 1998, 290:444-459.) can be provided; (iii) the heterologous signal sequences is chosen and/or inserted such that it acts as intrapolypeptide chaperones to prevent rapid folding; and/or (iv) the DT or CRM197 is modified such that it contains features in its final structure (e.g., disulfide bonds) that do not form in the environment of the cytoplasm so that the proteins cannot attain their final folded conformations in the cytoplasm.

5.2.1 Signal Peptides

Illustrative heterologous signal peptides that can be used with the methods provided herein are: the *E. coli* DsbA signal sequence, the MalE, OmpA, and PelB signal peptides. Without being bound by theory, the choice of signal peptide can determine the secretion route, e.g., SRP-dependent vs. SecB dependent route to the translocon. The optimal expression conditions may differ for different targeting pathways. There are reports claiming technologies that allow the identification of the targeted secretion pathway (Marricchi M, Camacho L, Russell D G, DeLisa M P: Genetic toggling of alkaline phosphatase folding reveals signal peptides for all major modes of transport across the inner membrane of bacteria. J Biol Chem 2008, 283(50):35223-35235).

The preferred signal peptides are selected from known and predicted, secreted proteins which are efficiently exported to the periplasm of *E. coli* via co-translational pathways. Among others, the signal peptides of *E. coli* heat-labile enterotoxin, *E. coli* outer membrane porin A (OmpA), *E. coli* maltose binding protein (MalE), *E. carotovorans* pectate lyase (PelB), or *Bacillus* sp. endoxylanase (XynA) can be used.

5.2.2 Cleavage Sites

Without being bound by theory, signal peptides are cleaved off the preprotein by a signal peptidase, and in *E. coli* there are SPaseI and II. SPaseI is cleaving most soluble and some membrane protein signal peptides, whereas SPaseII cleaves signal peptides from lipoproteins. SPaseI is the signal peptidase responsible in the presented invention. SPaseI usage could be determined (Paetzel M, Karla A, Strynadka N C, Dalbey R E: Signal peptidases. Chemical reviews 2002, 102(12):4549-4580).

Without being bound by theory, cleavage site locations are defined by i) the structure of the characteristic signal peptide organization with a hydrophobic core, a charged N terminus and a hydrophilic C terminus, and ii) by the primary sequence around the cleavage position (often A-X-A) (Heijne G: The distribution of positively charged residues in bacterial inner membrane proteins correlates with the trans-membrane topology. The EMBO journal 1986, 5(11): 3021-3027.). Both parameters are well understood and prediction programs have a high accuracy (Petersen T N, Brunak S, von Heijne G, Nielsen H: SignalP 4.0: discriminating signal peptides from transmembrane regions. Nat Methods 2011, 8(10):785-786). The program SignalP 4.0 server provides a cleavage probability based on the sequence of the first 70 amino acids of the pre-protein. In certain embodiments, engineered cleavage sites for use with the methods provided herein have a Y score of at least 0.4, 0.5, 0.6, 0.7, 0.72. 0.75, 0.8, 0.85, 0.9, or at least 0.95.

In certain embodiments, the signal peptide cleavage site is designed such that the predicted N-terminus is the N-terminus of the naturally existing protein. In other embodiments, the signal peptides and N terminus of the CRM197 are designed such that the N terminus is as close to the natively found N terminus as possible.

The natural N terminus after signal peptide cleavage of the CRM197 protein is GADDV (SEQ ID NO: 9) . . . (Bell C E, Eisenberg D: Crystal structure of nucleotide-free diphtheria toxin. Biochemistry 1997, 36(3):481-488). In certain specific embodiments, the N-terminus of CRM197 expressed in *E. coli* using the DsbA signal peptide can be:

MKKIWLALAGLVLAFS
ASA-(cleavage)-ADDVVDSSK (SEQ ID NO: 13) . . .
and using the PelB signal peptide
MKKIWLALAGLVLAFS
AMA-(cleavage)-GADDVVDSSKS (SEQ ID NO: 14) . . . .

Note the AXA motif at the cleavage site, where cleavage takes place after the second A.

Other cleavage sequences, and signal peptide cleavage site combinations are set forth in Table 2 below.

5.3 Expression Plasmids

A vast variety of expression vectors is known for recombinant expression in *E. coli* cells. In principle, any vector backbone can be used. Illustrative vectors are: pEC415 (Schulz H, Hennecke H, Thony-Meyer L: Prototype of a heme chaperone essential for cytochrome c maturation. Science 1998, 281(5380):1197-1200), pBR322 (Bolivar F, Rodriguez R L, Greene P J, Betlach M C, Heyneker H L, Boyer H W, Crosa J H, Falkow S: Construction and characterization of new cloning vehicles. II. A multipurpose cloning system. Gene 1977, 2(2):95-113), pBAD (Invitrogen corporation, Carlsbad, Calif.), pET series (Invitrogen), pUC series (Lin-Chao S, Chen W T, Wong T T: High copy number of the pUC plasmid results from a Rom/Rop-suppressible point mutation in RNA II. Mol Microbiol 1992, 6(22):3385-3393), pACT3, pEXT22, pEXT20 (Dykxhoorn D M, St Pierre R, Linn T: A set of compatible tac promoter expression vectors. Gene 1996, 177(1-2):133-136.), pBLUESCRIPT series (Stratagene, Agilent Technologies, Santa Clara, Calif.), pGEM series (Promega Corp., Madison, Wis.). All these vectors could be used for cloning the expression cassette of the preprotein under control of an inducible promoter.

Illustrative plasmids are provided as SEQ ID NOs: 1 and 2. The vector backbone is based on pBR322 containing a medium to high copy pMB1 origin of replication, an ampicillin resistance cassette which can be exchanged by a kanamycin cassette, the regulon of the araBAD operon encoding the AraC repressor and the araBAD promoter for high level protein expression induction.

In certain embodiments, a target protein, e.g., CRM197 or DT, is expressed from chromosomally integrated constructs. This strategy requires additional technologies which are well known to those skilled in the art and would result in a genome-integrated expression construct consisting of the same elements as an expression plasmid but not requiring the selection cassette (only for selection upon genomic integration) and the origin of replication.

5.4 Promoters

Among well-known high expression inducible promoters, any can be used that is functional at the temperature for expression of the protein of interest. In certain embodiments, a promoter to be used with the methods provided herein is active below the temperature of 37° C., below 36° C., 35° C., 34° C., 33° C., 32° C., 31° C., or below 30° C. The following list contains illustrative bacterial expression promoters that can be used with the methods provided herein (Table 1):

TABLE 1

Inducible promoters used in bacterial expression (Source: website of the: The Wolfson Centre for Applied Structural Biology of the Hebrew University of Jerusalem)

| Promoter | Source | Regulation | Induction | Level of Expression | Additional Information |
|---|---|---|---|---|---|
| lac | E. coli | lacI, lacI$^q$ * | IPTG | low | |
| lacUV5 | E. coli | lacI, lacI$^q$ * | IPTG | low | Theoretically not subject to cAMP dependent regulation |
| tac (hybrid) | E. coli | lacI, lacI$^q$ * | IPTG | Allows accumulation of protein to about 15-30% of total cell protein | Consists of the −35 region of the trp promoter and the −10 region of the lac promoter (differs from the trc promoter by 1 bp) |
| trc (hybrid) | E. coli | lacI, lacI$^q$ * | IPTG | Allows accumulation of protein to about 15-30% of total cell protein | Consists of the −35 region of the trp promoter and the −10 region of the lac promoter (differs from the tac promoter by 1 bp) |
| trp | E. coli | Addition of fructose to the growth medium increases down regulation under non-induced conditions. | Tryptophan starvation or addition of B-indoleacrylic acid | | |
| araBAD | E. coli | araC | l-arabinose | Weaker than the tac promoter | There is extensive heterogeneity in cell populations treated with subsaturating concentrations of l-arabinose (some bacteria are fully induced and others not at all). |
| phoA | E. coli | phoB (positive) phoR (negative) | phosphate starvation | | Tightly controlled. Induction requires phosphate starvation, and so can limit the duration of protein synthesis. |
| recA | E. coli | lexA | nalidixic acid | | |
| proU | E. coli | | osmolarity | | |
| cst-1 | E. coli | | glucose starvation | | |
| tetA | E. coli | | tetracyclin | | |
| cadA | E. coli | cadR | pH | | |
| nar | E. coli | fnr | anearobic conditions | | |
| cspA | E. coli | | Thermal cold shock (shift to below 20° C.) | | The cspA core promoter is only weakly induced by temperature downshift. A 159 nucleotide long untranslated region at the 5' end of cspA driven transcripts makes them highly unstable at 37° C. and significantly increases their stability at low temps. This region also favors their engagement by cold modified translational machinery. The cspA system becomes repressed 1-2 hours after temperature downshift. |
| SP6 | Salmonella phage | | | | |
| T7 | T7 phage | cIts857 | thermal | | |
| T7-lac operator | T7 phage | lacI$^q$ * | IPTG | Allows accumulation of protein to about 40-50% of total cell protein | |
| T3 lac operator | T3 phage | lacI$^q$ * | IPTG | | |
| T5-lac operator | T5 phage | lacI, lacI$^q$ * | IPTG | | This promoter is recognized by the E. coli RNA polymerase |

TABLE 1-continued

Inducible promoters used in bacterial expression (Source: website of the: The Wolfson Centre for Applied Structural Biology of the Hebrew University of Jerusalem)

| Promoter | Source | Regulation | Induction | Level of Expression | Additional Information |
|---|---|---|---|---|---|
| T4 gene 32 | T4 phage | | T4 infection | | |
| nprM-lac operator | Bacillus | lacI$^q$ * | IPTG | | |
| VHb | Vitreoscilla | | oxygen | | |

5.5 Culture Medium

Culture medium for protein production can be any defined, semi-defined or complex medium suitable for overexpression of recombinant proteins in E. coli. A rich complex medium like terrific broth (TB) is preferred, but defined mineral salts media may also be used. Terrific broth is composed of 24 g/l yeast extract, 12 g/l tryptone or peptone (i.e. proteolytically digested casein, soy protein or other protein), and 4% (v/v) glycerol. In addition, the medium is buffered.

In certain specific embodiments, the concentration of Magnesium ions is at most 10 nM, 50 nM, 100 nM, 250 nM, 500 nM, 750 nM, or at most 1 mM. In certain specific embodiments, no Magnesium is added. In certain specific embodiments, no $MgCl_2$ is added to the culture medium.

In certain specific embodiments, the pH of the culture medium is between 6 and 9. In certain specific conditions, yeast extract can be present in the culture medium at a concentration of between 10-30 g/l. In certain specific embodiments, the culture medium comprises glycerol from 2.5% to 10%. In certain other embodiments, the culture medium comprises glycerol at least 5%, 10%, 15%, or at least 20%.

5.6 Induction and Expression

Expression cultures before induction can be grown at different temperatures, for example, temperatures ranging from 4-35° C. or 18-37° C. In certain embodiments, expression cultures before induction are grown at a temperature within the range of 18-20° C., 20-22° C., 22-24° C., 24-26° C., 26-28° C., 28-30° C., 30-32° C., 32-34° C., or 34-36° C. In certain embodiments, expression cultures before induction are grown at a temperature of about 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., or 37° C.

Cultivation temperatures after induction can fall into certain ranges, for example, temperatures ranging from 4-35° C. or 18-37° C., and can be different from the before induction conditions. For example, a pre-induction culture can be grown at higher temperatures, e.g., a temperature described above, and then shifted to a lower temperature, e.g., a temperature in the range of 15-30° C., for production. In certain embodiments, cultures after induction are grown at a temperature within the range of 18-20° C., 20-22° C., 22-24° C., 24-26° C., 26-28° C., 28-30° C., 30-32° C., 32-34° C., or 34-36° C. In a specific embodiment, said temperature falls within a range that is lower than the range at which the pre-induction culture is grown. In certain embodiments, cultures after induction are grown at a temperature of about 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., or 37° C. In a specific embodiment, said temperature falls within a range that is lower than the range at which the pre-induction culture is grown.

Depending on the construct, expression time can be from 2-20 hrs. Inducer concentrations are, dependent on the promoter, from 0.01 to 1% (w/v) arabinose (ParaBAD), or from 10 to 1000 µM IPTG. Induction can be done at OD600 values obtained during fermentation between 0.3 to 1.5 in shake flask cultures, and at OD600 between 5 to 200 in bioreactor fermentations. In certain specific embodiments, induction is done at an OD600 of between 5 and 50, 25 and 75, 50 and 100, 75 and 125, 100 and 150, 125 and 175, 150 and 200, or 175 and 200. In certain embodiments, induction is done at the beginning of the log phase in shake flask. Bioreactor fermentations may be done at constant pO2 values ranging from 0% to 40%. pO2 regulation may be done by regulating stirrer speed or aeration rate.

In certain embodiments, the promoter is inducible with arabinose; arabinose concentrations can be at least 0.01, 0.05, 0.1, 0.2, 0.3, 0.4, 0.5, 0.6, 0.7, 0.8, 0.9, or at least 1% (w/v) arabinose. In certain embodiments, concentration of the inducer arabinose is at most 0.01, 0.05, 0.1, 0.2, 0.3, 0.4, 0.5, 0.6, 0.7, 0.8, 0.9, or at most 1% (w/v) arabinose In certain embodiments, the promoter is inducible with IPTG; IPTG concentrations can be at least 10, 25, 50, 75, 100, 200, 250, 300, 400, 500, 600, 700, 750, 800, 900 or at least 1000 µM IPTG. In certain embodiments, concentration of the inducer IPTG is at most 10, 25, 50, 75, 100, 200, 250, 300, 400, 500, 600, 700, 750, 800, 900 or at most 1000 µM IPTG.

In certain embodiments, expression is performed in shake flask cultures. $OD_{600}$ values at the time of induction are at least 0.3, 0.4, 0.5, 0.6, 0.7, 0.8, 0.9, 1, 1.1, 1.2, 1.3, 1.4, or at least 1.5 in shake flask cultures. In certain embodiments, $OD_{600}$ values at the time of induction are at most 0.3, 0.4, 0.5, 0.6, 0.7, 0.8, 0.9, 1, 1.1, 1.2, 1.3, 1.4, or at most 1.5 in shake flask cultures.

In certain embodiments, expression is performed in bioreactor fermentations. OD600 values at the time of induction are at least 5, 10, 15, 20, 25, 50, 75, or at least 100 in bioreactor fermentations. In certain embodiments, $OD_{600}$ values at the time of induction are at most 5, 10, 15, 20, 25, 50, 75, or at most 100 in bioreactor fermentations.

Bioreactor fermentations can be performed at constant pO2 values of at least 1%, 2%, 3%, 4%, 5%, 6%, 7%, 8%, 9%, 10%, 15%, 20%, 25%, 30%, 35%, or at least 40%. In certain embodiments, bioreactor fermentations can be performed at constant pO2 values of at most 1%, 2%, 3%, 4%, 5%, 6%, 7%, 8%, 9%, 10%, 15%, 20%, 25%, 30%, 35%, or at most 40%.

5.7 Host Cells

Expression strains for recombinant production of the target protein can be but are not limited to E. coli K12 and B strains, like W3110, DB1, DH5a, BL21, BL21(DE3), C43, JM109, JM101, JM110, and derivatives thereof (Huang C J, Lin H, Yang X: Industrial production of recombinant therapeutics in *E. coli* and its recent advancements. Journal of Industrial Microbiology & Biotechnology 2012, 39(3):383-399). Host cells may be chromosomally modified to accommodate optimal expression of the CRM197 protein. For example, periplasmic proteases like DepP, Prc, Spr, and/or protease III may be deleted in production strains. Deletions may be useful alone or in combinations with other proteases. In addition, suppressor mutations like for example sprW148R (Chen C, Snedecor B, Nishihara J C, Joly J C, McFarland N, Andersen D C, Battersby J E, Champion K M: High-level accumulation of a recombinant antibody fragment in the periplasm of *E. coli* requires a triple-mutant (degP prc spr) host strain. Biotechnology and bioengineering 2004, 85(5):463-474.) may increase CRM197 protein yield.

5.8 Assays

Methods to characterize yield, purity, stability, nicking degree, toxicity, endotoxin content are well established and define the quality for use of CRM197 in a vaccine. Analysis of CRM197 is done by, e.g., high performance size exclusion chromatography, isoelectric focusing, SDS-PAGE and Western Blot, molecular weight determination by MS, N terminal sequencing, amino acid analysis, reverse phase liquid chromatography, electrospray mass spectroscopy, and peptide mapping by mass spectroscopy after tryptic digestion.

Analytical methods are described and parameters that define acceptable quality are well established for use in medicinal products. Detailed information and framework parameters are given e.g., in the guidelines released by the European medicinal agency, EMEA and can be found at EMEA's website, e.g., for the CRM197-containing vaccine Prevenar.

5.8.1 Concentration of Expression Product

Standard protein concentration technologies like the Lowry assay, BCA assay, and Bradford assays could be used, as well as determination of the UV absorption at 280 nm and quantification from Coomassie stained SDS-PAGE gels by densitometry or capillary gel electrophoresis by fluorescent dye intensity measurements.

5.8.2 Folding of Expression Product

Folding of the product can be analyzed directly by circular dichroism spectroscopy, protein NMR spectroscopy, and HPSEC. Indirect methods include solubility measurement, protease resistance, and activity assays for toxicity in the case of the DT A fragment, and binding assays for the CRM197 and DT B fragments.

5.8.3 Inclusion Bodies of Expression Product

Inclusion body formation is easily quantified by first homogenization of the harvested cells after fermentation, low spin centrifugation for sedimentation of the insoluble matter, and comparing pellet and supernatant side by side in an equivalent optical density manner. Intensity of the protein band allows estimation of the proportion in supernatant (soluble protein) and pellet (insoluble aggregates and inclusion bodies).

5.8.4 Solubility of Expression Product

Supernatant solution containing the protein can be centrifuged and sterile filtered. If the protein remains in solution and is not depleted from the filtrate and supernatants, the protein is soluble. A more sophisticated method is dynamic light scattering. It allows the determination of particle size, which is indicative of the oligomeric or micro aggregated state of the purified protein.

Solubility is inversely proportional to aggregate formation such that a finding of high solubility demonstrates no or low level of aggregate formation.

5.8.5 Periplasmic Localization of Expression Product

Periplasmic localization is measured by fractionation of cells and comparing specific protein yields observed in periplasm and spheroplast fractions. Fractionation is done by using the sucrose-lysozyme method (Kowarik M, Young N M, Numao S, Schulz B L, Hug I, Callewaert N, Mills D C, Watson D C, Hernandez M, Kelly J F et al: Definition of the bacterial N-glycosylation site consensus sequence. The EMBO journal 2006, 25(9):1957-1966), osmotic shock (Johansson H J, Jagersten C, Shiloach J: Large scale recovery and purification of periplasmic recombinant protein from *E. coli* using expanded bed adsorption chromatography followed by new ion exchange media. J Biotechnol 1996, 48(1-2):9-14.), or polymyxin (Schulz H, Hennecke H, Thony-Meyer L: Prototype of a heme chaperone essential for cytochrome c maturation. Science 1998, 281(5380): 1197-1200). Fraction aliquots are normalized based on sample volumes and culture $OD_{600}$ and analyzed by SDS PAGE and Western blotting.

5.8.6 Cleavage of Signal Sequence

Cleavage of signal peptides is assayed by i) gel shift analysis of fractionated cells as described in 5.8.5. In this analysis, unprocessed pre-protein may be accumulating in cytoplasmic aggregates or membranes, and processed protein will be present in soluble, periplasmic fractions. Different electrophoretic mobility will constitute a shift between processed and unprocessed pre-proteins by SDS-PAGE (and Western blot if necessary). Eventually, N-terminal amino acid sequencing can be used to determine the processed N-terminus and thereby define the cleavage site experimentally.

5.8.7 Potential Toxicity of CRM197

CRM197 can be tested for the presence of active toxin by measuring the ADP-ribosyl transferase activity. Additionally, other tests (cytotoxicity in HeLa cells or Vero cells in vitro, lethality in guinea pigs in vivo, abnormal toxicity test) can be used to demonstrate the nontoxicity of CRM197

5.9 Compositions

Diphtheria toxin, nontoxic forms of diphtheria toxin, e.g., CRM197, produced in accordance with the methods provided herein can be further processed to immunogenic compositions or vaccines. For example, the protein can be conjugated to an oligosaccharide or a polysaccharide to yield an immunogenic composition or vaccine. In certain, specific embodiments, such an immunogenic composition or vaccine has improved immunogenic properties over prior art compositions. Without being bound by theory, the methods provided herein provide a more homogenous population of soluble CRM197 protein. As such any immunogenic composition or vaccine is more effective than prior art compositions.

In certain embodiments, provided herein is a composition comprising a diphtheria toxin, nontoxic forms of diphtheria toxin, e.g., CRM197, that has been produced in accordance with the methods provided herein. In certain more specific embodiments, such a composition is a pharmaceutical com-

6 EXAMPLES

6.1 Example 1

Different experimental setups were tested and the CRM197 yield was determined by Western blotting using anti diphtheria toxin antiserum for detection of CRM197.

A DNA open reading frame for CRM197 expression was synthesized by a commercial provider (Genescript, Piscataway, N.J.) in a codon optimized fashion containing the N-terminal signal peptide of the DsbA protein of *E. coli* instead of the natural signal peptide, and a C terminal hexa-histidine tag. The resulting protein sequence is SEQ ID 5. The open reading frame for ssDsbA-CRM197-his6 was inserted into the NdeI and XbaI sites of pEC415 (Schulz H, Hennecke H, Thony-Meyer L: Prototype of a heme chaperone essential for cytochrome c maturation. Science 1998, 281(5380):1197-1200).

From this plasmid, various mutants were made to analyze the differences of the CRM197 yields. Mutations were introduced at the expected signal peptide cleavage site by quick change mutagenesis as described by the manufacturer (Stratagene, Agilent Technologies, Santa Clara, Calif.). The resulting constructs are summarized in Table 1.

The mentioned plasmids were transformed into BL21 and W3110 cells to perform protein expression experiments. Transformed colonies were picked from an LB plate and used to inoculate LB medium liquid culture, which were grown over night at 37° C. The high density cultures were diluted to an $OD_{600}$ of 0.05 into fresh LB medium and grown further until the OD reached a value of $OD_{600}$=0.5. Then arabinose was added for induction of recombinant protein expression. Initial experiments using some of the mentioned constructs were performed under various conditions.

However, no CRM197 protein was detected in cellular extracts when compared to control cells expressing no protein or expressing EPA (Ihssen J, Kowarik M, Dilettoso S, Tanner C, Wacker M, Thony-Meyer L: Production of glycoprotein vaccines in *E. coli*. Microbial cell factories 2010, 9:61). Neither at 30 nor 37° C., using overnight induction times and LB medium supplemented with ampicillin for plasmid maintenance.

Subsequently, expression was conducted as follows. For the expression, high density cultures from overnight incubations were diluted into terrific broth for better cell viability. Cultures were grown until exponential phase and induced for 2 hours and overnight, and then cells were harvested and cellular extracts prepared by dissolving OD equivalent amounts of biomass in Lämmli sample buffer. The extracts were separated by SDS PAGE and electrotransferred to nitrocellulose membranes for subsequent immunodetection using anti DT and anti his tag antisera. Surprisingly, a protein signal at the expected electrophoretic mobility of CRM197 at about 60 kDa was detected after 2 hours of induction. Expression constructs p932, p934, and p722 led to detectable signals in anti DT and anti his tag antiserum immunoblots. p932 appeared to produce most, p934 less, and p722 even lesser CRM197 signals. A control extract from cells containing an expression plasmid lacking a signal peptide sequence showed CRM197 at the correct molecular weight range and confirmed the identity of the material in the other lanes.

These experiments showed that CRM197 could be expressed, but not whether it was soluble or folded. As indicated in FIG. 1, CRM197 without a signal peptide was detected and expected in cytoplasmic inclusion bodies. The expected yields are unknown and can only be estimated by comparison to the expression of EPA. In this comparison, CRM197 reaches yields similar to EPA based on the signal intensities observed using anti his tag antiserum Western blotting as illustrated in FIG. 1 (compare lanes 4A and 4B to 5A and 5B). EPA in controlled bioreactor fermentations leads to up to 0.5 g/l protein.

The order of efficiency for CRM197 production was p932>p934>p722. The methionine residue encoded in the cleavage site from the CRM197 expressed from p722 may interfere with productivity, and also the glycine residue has some influence. It appears, however, that formation of an N terminus of CRM197 with one amino acid less (ADDV . . . ; p932) than the natural N terminus in combination with the serine residue at the −2 position relative to the cleavage site leads to the optimal expression context when the DsbA signal peptide is used.

However, it was possible to detect CRM197 signals in expression experiments using different expression constructs and TB medium.

6.2 Example 2

Figure 2:
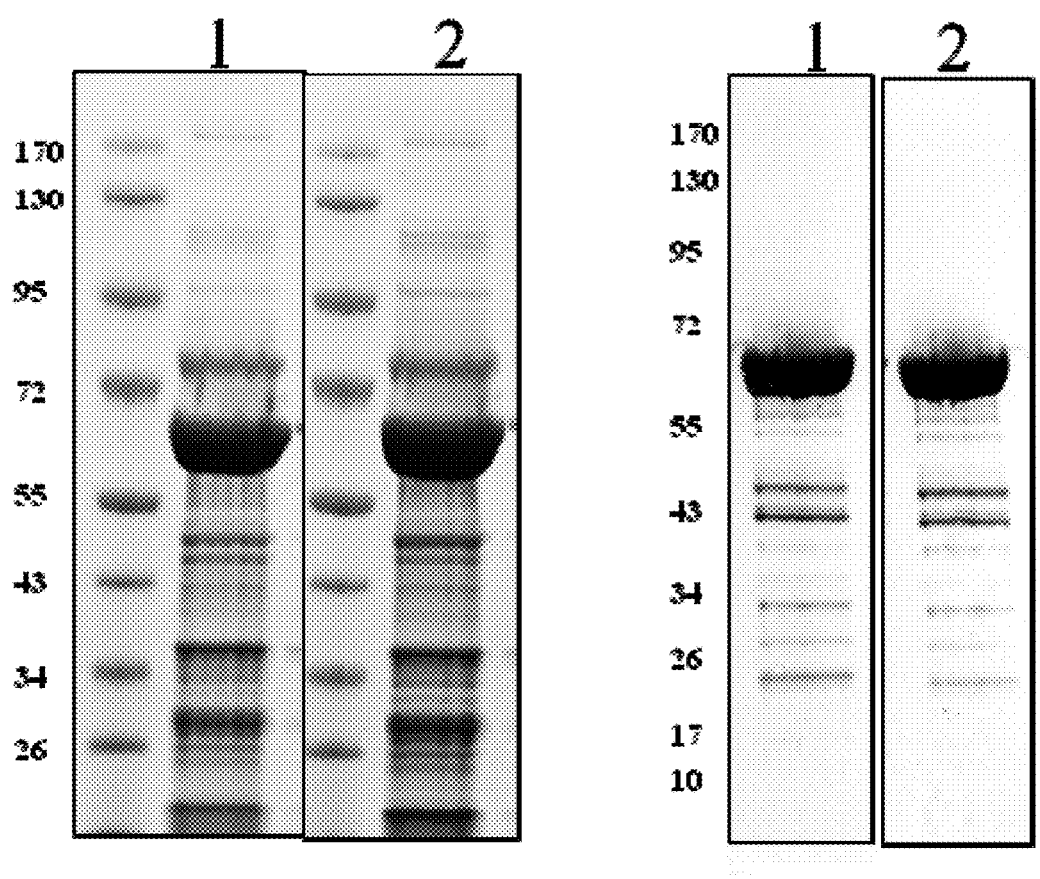

To analyze solubility and overall yield in shake flasks, CRM197 was purified from cell cultures using two different expression constructs. Expression strain was BL21, the expression plasmids p932 or p933. 5 liter shake flasks containing 1 l TB supplemented with ampicillin were inoculated with a pre-culture grown in LB supplemented with ampicillin and cultured at 30° C. At $OD_{600}$ of 0.5, arabinose was added to 0.2% (w/v) and expression allowed for 2 (p932) or 4 hours (p933). Cells were then harvested by centrifugation, resuspended in buffer for periplasma extraction (20% w/v sucrose, 30 mM Tris HCl pH 8.0, 1 mM EDTA, 1 mg/ml lysozyme, 1 tablet/80 mL Complete protease inhibitor mix (Roche, Basel, Switzerland)) at a ratio of 20 OD per ml, incubated on ice for 30 min, and centrifuged for 15 min at 8000 rpm and 4° C. The supernatant was further treated with DNase (Fluka, Balgach, Switzerland), centrifuged at 4° C., and the supernatant sterile filtered. The filtrate was prepared for purification using Ni2+ affinity chromatography. Load, wash and elution were performed at specific imidazole concentrations (10, 20, 500 mM). Elution fractions were analyzed by SDS PAGE and Coomassie brilliant blue staining (FIG. 2).

A major band corresponding to CRM197 was detected in elution fractions from the purification. Protein determination resulted in values of about 2 mg protein from construct p932, and about 4 mg from construct p933 per liter fermentation broth. N terminal sequencing and MALDI MSMS of excised protein bands from this SDS PAGE gel confirmed the N terminus of CRM197 in both cases (see Table 1) and that the protein is indeed CRM197.

The difference between protein expressed from p932 and p933 is the signal peptide sequence and the resulting mature N-terminus of CRM197. p933 produced the correct wild type N terminus; although the Y score for cleavage efficiency is lower than for p932. In FIG. 1, p934 borne expression appears to be even less efficient, and accordingly, the Y score is less. Thus a combination of a high Y score value and a signal peptide cleavage position resulting in the native N-terminus GADDV (SEQ ID NO: 9) seems to be the optimal configuration for high yield CRM197 expression in

*E. coli.* Expression time, temperature, medium and inducer concentration may influence signal peptide cleavage yield, speed, and efficiency and accordingly CRM197 yields.

6.3 Example 3

Figure 3:
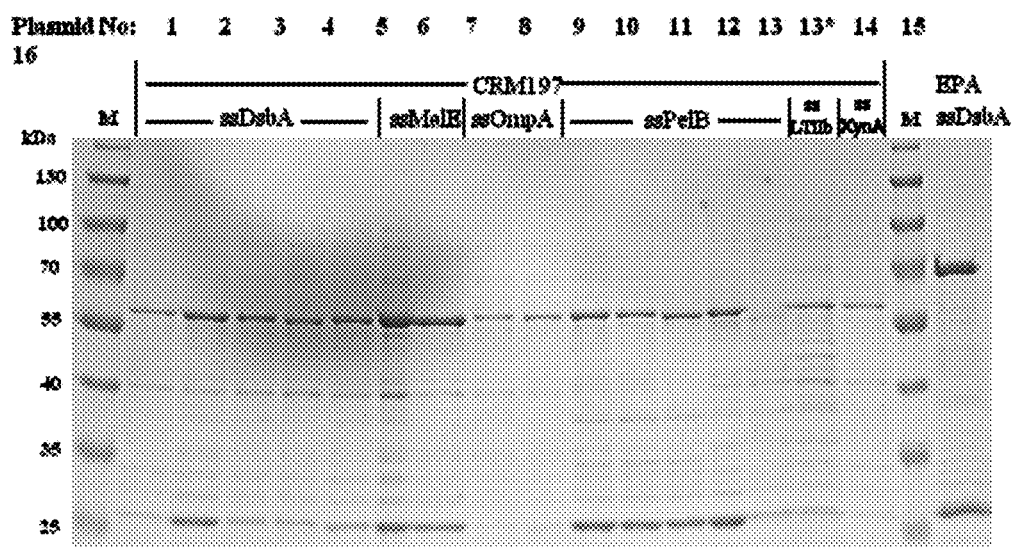

To analyze the productivity of different constructs in parallel, small scale shake flask expression experiments were performed, the periplasmic extracts were prepared and analyzed by SDS PAGE for the CRM197 band intensity by Coomassie staining (FIG. 3) and quantified (Table 2). The detailed expression conditions are given in the legend of FIG. 3 and in Table 2.

DsbA, MalE, and PelB signal peptides resulted in the best yields in combination with optimized expression conditions. The expression conditions had a stronger influence on yields than the signal peptide cleavage site configurations. However, the importance of signal peptide cleavage site sequence is shown e.g., by the low yields obtained with the p722 expression plasmid (at 25° C.). Although p722 encodes the DsbA signal, the yield is low compared to other sequences (encoded in e.g., p932, p933, p934, or p936). Signal peptide cleavage site configurations can be classified according to their yield efficiencies: ASA-ADD (SEQ ID NO: 15) and AMA-GADD (SEQ ID NO: 16) appear better than ASA-GADD (SEQ ID NO: 17), and AMG-ADD (SEQ ID NO: 18) being the least efficient site. Y scores do not correlate with expression levels.

All tested constructs containing the PelB signal resulted in high yields at 30° C. expression temperature. Differences in the signal peptide cleavage site sequence did not drastically influence yields. However, the differences in signal peptide cleavage site sequence were small in this set of constructs.

TABLE 2

Plasmids and signal peptides used for periplasmic expression of CRM197 and a well-secreted reference protein (EPA-6H). Plasmids were transformed in *E. coli* (W3110 derived strain) and cultivated in TB medium at temperatures yielding the highest levels of recombinant proteins. Samples for preparation of periplasmic extracts were taken 4 h after induction with 4 g L$^{-1}$ L-arabinose, concentration of resuspended cells in sucrose-lysozyme extraction buffer was normalized to OD$_{600}$ = 20. Concentrations of overexpressed recombinant proteins in periplasmic extracts were estimated by image analysis of a Coomassie-stained SDS-PAGE gel using marker bands at 55 kDa as reference. Protein yields in shake flasks were back calculated via OD$_{600}$ at the time of sampling.

| Plasmid No. | Name GVXN | Protein SEQ ID | Signal peptide | Predicted cleavage site (SEQ ID NO: ) | Cleavage probability (Y score Signal P 4.0) | Determined N-terminus after export | C-terminal 6xHis tag | Optimal expression temperature | Protein conc. (CRM197/EPA) in periplasmic extracts (μg mL$^{-1}$) | OD$_{600}$ at sampling | Protein yield in shake flask (mg L$^{-1}$) |
|---|---|---|---|---|---|---|---|---|---|---|---|
| \multicolumn{12}{c}{Plasmids for periplasmic expression of CRM197, backbone pEC415} |
| 1 | p722 | 5 | DsbA | AFSAMG-ADDV (19) | 0.763 | n.a. | yes | 25° C. | 24 | 1.28 | 1.6 |
| 2 | p932 | 2 | DsbA | AFSASA-ADDV (20) | 0.878 | ADDV . . . | yes | 25° C. | 66 | 2.66 | 8.8 |
| 3 | p933 | 4 | DsbA | AFSAMA-GADDV (21) | 0.783 | GADDV . . . | yes | 25° C. | 51 | 1.30 | 3.3 |
| 4 | p936 | x | DsbA | AFSAMA-GADDV (22) | 0.783 | n.a. | no | 20-25° C. | 57 | 1.62 | 4.6 |
| 5 | p934 | x | DsbA | AFSASA-GADDV (23) | 0.681 | n.a. | yes | 25° C. | 64 | 1.38 | 4.4 |
| 6 | p1027 | x | MalE | SASALA-MGADDV (24) | 0.722 | n.a. | yes | 25° C. | 97 | 1.43 | 6.9 |
| 7 | p1029 | x | MalE | SASALA-ADDV (25) | 0.894 | n.a. | yes | 25° C. | 93 | 1.54 | 7.1 |
| 8 | p1030 | x | OmpA | ATVAQA-MGADDV (26) | 0.790 | n.a. | yes | 25° C. | 9 | 1.53 | 0.7 |
| 9 | p1032 | x | OmpA | ATVAQA-ADDV (27) | 0.898 | n.a. | yes | 25° C. | 11 | 1.54 | 0.9 |
| 10 | p1033 | x | PelB | AQPAMA-MGADDV (28) | 0.878 | n.a. | yes | 30° C. | 36 | 3.29 | 5.9 |
| 11 | p1018 | x | PelB | AQPAMA-GADDV (29) | 0.874 | n.a. | yes | 30° C. | 27 | 3.72 | 5.0 |
| 12 | p1035 | x | PelB | AQPAMA-ADDV (30) | 0.874 | n.a. | no | 30° C. | 32 | 3.96 | 6.4 |
| 13 | p1036 | x | PelB | AQPAMA-AGADDV (31) | 0.918 | n.a. | yes | 30° C. | 44 | 3.27 | 7.2 |
| 14 | p938 | x | LT-IIb* | SVQAHA-GADDV (32) | 0.885 | n.a. | yes | 30° C. | 13 | 1.11 | 0.7 |
| 15 | p1039 | x | XynA | SATASA-MGADDV (33) | 0.464 | n.a. | yes | 25° C. | 13 | 0.94 | 0.6 |
| \multicolumn{12}{c}{Reference plasmid for periplasmic expression of EPA, backbone pEC415} |
| 16 | p150 | — | DsbA | AFSASA-AEEA (34) | 0.873 | AEEA . . . | yes | 30° C. | 73 | 2.58 | 9.4 | n.a.: not analyzed.
*E. coli* heat-labile enterotoxin type IIb, chain B

7 SEQUENCES

```
SEQ ID 1: p932
GTCGAGCTAGTAAAAGCATTTTAAATAAGGAGGAATAACACATATGAAAAAGATTTGGCT

GGCGCTGGCTGGTTTAGTTTTAGCGTTTAGCGCCAGCGCCGCAGATGACGTTGTTGACAG

CAGCAAATCCTTCGTTATGGAAAACTTCTCCTCTTATCACGGCACCAAACCGGGCTATGT

GGACAGCATTCAGAAAGGTATCCAAAAACCGAAATCTGGCACGCAGGGTAACTACGATGA

CGATTGGAAAGAATTCTACAGCACCGACAACAAATATGATGCGGCCGGTTACTCAGTTGA
```

-continued

```
CAACGAAAATCCGCTGTCGGGCAAAGCCGGCGGTGTGGTTAAAGTCACGTATCCGGGCCT

GACCAAAGTCCTGGCCCTGAAAGTGGATAATGCAGAAACCATCAAAAAAGAACTGGGTCT

GAGCCTGACGGAACCGCTGATGGAACAGGTTGGCACCGAAGAATTTATCAAACGCTTCGG

CGATGGTGCCAGTCGTGTCGTGCTGTCCCTGCCGTTCGCAGAAGGTAGCTCTAGTGTCGA

ATATATTAACAATTGGGAACAAGCGAAAGCCCTGTCCGTGGAACTGGAAATCAACTTTGA

AACCCGCGGCAAACGTGGTCAGGATGCGATGTATGAATACATGGCACAAGCTTGCGCGGG

TAATCGCGTTCGTCGCAGCGTCGGCTCCTCACTGTCTTGTATCAACCTGGACTGGGATGT

TATCCGTGATAAAACCAAAACGAAAATCGAAAGTCTGAAAGAACACGGCCCGATCAAAAA

CAAAATGAGCGAATCTCCGAATAAAACGGTGTCCGAAGAAAAAGCTAAACAGTATCTGGA

AGAATTCCACCAAACCGCACTGGAACATCCGGAACTGTCAGAACTGAAAACCGTCACGGG

TACCAACCCGGTGTTTGCCGGCGCAAATTACGCAGCTTGGGCTGTGAACGTTGCGCAAGT

GATTGACTCGGAAACGGCCGATAATCTGGAAAAAACCACGGCGGCCCTGAGTATTCTGCC

GGGCATCGGTTCCGTGATGGGTATTGCCGATGGCGCAGTTCATCACAACACCGAAGAAAT

TGTCGCCCAGTCTATCGCACTGTCGAGCCTGATGGTTGCTCAAGCGATTCCGCTGGTTGG

CGAACTGGTTGATATCGGCTTTGCAGCTTACAACTTCGTGGAAAGTATCATCAACCTGTT

TCAGGTTGTCCATAACTCATATAATCGCCCGGCCTACTCGCCGGGTCACAAAACCCAACC

GTTCCTGCATGACGGCTACGCGGTTAGCTGGAATACGGTCGAAGATTCTATTATCCGTAC

CGGCTTTCAGGGTGAATCTGGCCACGACATTAAAATCACGGCTGAAAACACCCCGCTGCC

GATTGCCGGTGTTCTGCTGCCGACCATCCCGGGTAAACTGGATGTGAATAAATCAAAAAC

CCATATCTCGGTTAACGGTCGCAAAATTCGTATGCGCTGCCGTGCGATCGACGGCGATGT

GACCTTCTGTCGTCCGAAAAGCCCGGTCTATGTGGGCAACGGTGTTCATGCTAATCTGCA

CGTCGCGTTTCATCGCTCTAGTTCCGAAAAAATCCACAGTAACGAAATCTCATCGGACTC

CATTGGTGTGCTGGGCTACCAGAAAACGGTGGATCATACCAAAGTTAATAGCAAACTGTC

ACTGTTCTTCGAAATCAAATCAGGCTCGCATCATCATCATCACCACTAATCTAGAGGATC

CCCGGGTACCGAGCTCGAATTCTTGAAGACGAAAGGGCCTCGTGATACGCCTATTTTTAT

AGGTTAATGTCATGATAATAATGGTTTCTTAGACGTCAGGTGGCACTTTTCGGGGAAATG

TGCGCGGAACCCCTATTTGTTTATTTTTCTAAATACATTCAAATATGTATCCGCTCATGA

GACAATAACCCTGATAAATGCTTCAATAATATTGAAAAAGGAAGAGTATGAGTATTCAAC

ATTTCCGTGTCGCCCTTATTCCCTTTTTTGCGGCATTTTGCCTTCCTGTTTTTGCTCACC

CAGAAACGCTGGTGAAAGTAAAAGATGCTGAAGATCAGTTGGGTGCACGAGTGGGTTACA

TCGAACTGGATCTCAACAGCGGTAAGATCCTTGAGAGTTTTCGCCCCGAAGAACGTTTTC

CAATGATGAGCACTTTTAAAGTTCTGCTATGTGGCGCGGTATTATCCCGTGTTGACGCCG

GGCAAGAGCAACTCGGTCGCCGCATACACTATTCTCAGAATGACTTGGTTGAGTACTCAC

CAGTCACAGAAAAGCATCTTACGGATGGCATGACAGTAAGAGAATTATGCAGTGCTGCCA

TAACCATGAGTGATAACACTGCGGCCAACTTACTTCTGACAACGATCGGAGGACCGAAGG

AGCTAACCGCTTTTTTGCACAACATGGGGGATCATGTAACTCGCCTTGATCGTTGGGAAC

CGGAGCTGAATGAAGCCATACCAAACGACGAGCGTGACACCACGATGCCTGCAGCAATGG

CAACAACGTTGCGCAAACTATTAACTGGCGAACTACTTACTCTAGCTTCCCGGCAACAAT

TAATAGACTGGATGGAGGCGGATAAAGTTGCAGGACCACTTCTGCGCTCGGCCCTTCCGG

CTGGCTGGTTTATTGCTGATAAATCTGGAGCCGGTGAGCGTGGGTCTCGCGGTATCATTG

CAGCACTGGGGCCAGATGGTAAGCCCTCCCGTATCGTAGTTATCTACACGACGGGGAGTC
```

-continued

```
AGGCAACTATGGATGAACGAAATAGACAGATCGCTGAGATAGGTGCCTCACTGATTAAGC

ATTGGTAACTGTCAGACCAAGTTTACTCATATATACTTTAGATTGATTTAAAACTTCATT

TTTAATTTAAAAGGATCTAGGTGAAGATCCTTTTTGATAATCTCATGACCAAAATCCCTT

AACGTGAGTTTTCGTTCCACTGAGCGTCAGACCCCGTAGAAAAGATCAAAGGATCTTCTT

GAGATCCTTTTTTTCTGCGCGTAATCTGCTGCTTGCAAACAAAAAAACCACCGCTACCAG

CGGTGGTTTGTTTGCCGGATCAAGAGCTACCAACTCTTTTTCCGAAGGTAACTGGCTTCA

GCAGAGCGCAGATACCAAATACTGTCCTTCTAGTGTAGCCGTAGTTAGGCCACCACTTCA

AGAACTCTGTAGCACCGCCTACATACCTCGCTCTGCTAATCCTGTTACCAGTGGCTGCTG

CCAGTGGCGATAAGTCGTGTCTTACCGGGTTGGACTCAAGACGATAGTTACCGGATAAGG

CGCAGCGGTCGGGCTGAACGGGGGGTTCGTGCACACAGCCCAGCTTGGAGCGAACGACCT

ACACCGAACTGAGATACCTACAGCGTGAGCTATGAGAAAGCGCCACGCTTCCCGAAGGGA

GAAAGGCGGACAGGTATCCGGTAAGCGGCAGGGTCGGAACAGGAGAGCGCACGAGGGAGC

TTCCAGGGGGAAACGCCTGGTATCTTTATAGTCCTGTCGGGTTTCGCCACCTCTGACTTG

AGCGTCGATTTTTGTGATGCTCGTCAGGGGGCGGAGCCTATGGAAAAACGCCAGCAACG

CGGCCTTTTTACGGTTCCTGGCCTTTTGCTGGCCTTTTGCTCACATGTTCTTTCCTGCGT

TATCCCCTGATTCTGTGGATAACCGTATTACCGCCTTTGAGTGAGCTGATACCGCTCGCC

GCAGCCGAACGACCGAGCGCAGCGAGTCAGTGAGCGAGGAAGCGGAAGAGCGCCTGATGC

GGTATTTTCTCCTTACGCATCTGTGCGGTATTTCACACCGCATGGTGCACTCTCAGTACA

ATCTGCTCTGATGCCGCATAGTTAAGCCAGTATACACTCCGCTATCGCTACGTGACTGGG

TCATGGCTGCGCCCCGACACCCGCCAACACCCGCTGACGCGCCCTGACGGGCTTGTCTGC

TCCCGGCATCCGCTTACAGACAAGCTGTGACCGTCTCCGGGAGCTGCATGTGTCAGAGGT

TTTCACCGTCATCACCGAAACGCGCGAGGCAGCTGCGGTAAAGCTCATCAGCGTGGTCGT

GAAGCGATTCACAGATGTCTGCCTGTTCATCCGCGTCCAGCTCGTTGAGTTTCTCCAGAA

GCGTTAATGTCTGGCTTCTGATAAAGCGGGCCATGTTAAGGGCGGTTTTTTCCTGTTTGG

TCACTGATGCCTCCGTGTAAGGGGATTTCTGTTCATGGGGTAATGATACCGATGAAAC

GAGAGAGGATGCTCACGATACGGGTTACTGATGATGAACATGCCCGGTTACTGGAACGTT

GTGAGGGTAAACAACTGGCGGTATGGATGCGGCGGGACCAGAGAAAAATCACTCAGGGTC

AATGCCAGCGCTTCGTTAATACAGATGTAGGTGTTCCACAGGGTAGCCAGCAGCATCCTG

CGATGCAGATCCGGAACATAATGGTGCAGGGCGCTGACTTCCGCGTTTCCAGACTTTACG

AAACACGGAAACCGAAGACCATTCATGTTGTTGCTCAGGTCGCAGACGTTTTGCAGCAGC

AGTCGCTTCACGTTCGCTCGCGTATCGGTGATTCATTCTGCTAACCAGTAAGGCAACCCC

GCCAGCCTAGCCGGGTCCTCAACGACAGGAGCACGATCATGCGCACCCGTGGCCAGGACC

CAACGCTGCCCGAGCGTCAACGGCGCCAGATACAGCAAACGGCTGCGGGGGAAATACGCG

GTTAAACGATCGACTGCCGCTTTGCCGCTGCGCCACAGCCGCCAGCATAGCCAGCCTCCG

ACCCACAGCAGCAACGCCGTCGCCAGCAGCAGCCATTTGAAATCTCCGCTCTGCATATCG

GAAGGAATATCGATTGCCGCTCCCGCCAGAATGCCCGGCAGGAAATAAAACGGCGGCCAC

AGCAAACAGCCAATCAAGTTCGGCCCAATAAATTTCGCCACGGGAAGATCCAGCATCCCT

GCCACCATCGGCACCAGCGGCCTCGTCGGACCGACAAAACGTCCGACCAGGATCGTGAAC

ATACTGTGCTGATGCAGCGCGTGTTCGGTTTTATCCAGCAGCGACTTGTTCTTTTTCATA

AAAGACCAGCGGTGTAGCGGCTTTTTAAAGCGCCACCCCAGCCAGAACGAAATCCAGTCG
```

-continued

```
CCCATCAGACAGCCGATAATACCCACCAGCCAGGCATGCCAAAAATTGAGCTCGCCGCTG
CCGATAAGCGCGCCCAGCCCCGCCATCAGTACCGTGCCGGGTAAAATCAACCCCACCAGC
GCCAGCGATTCCAGGAAGGCGACCAGCAACACGGCGATGAGCGAATACAGAGTGGATTGG
GTGATAAAGTGTTCCAGCAGTGCTTGCATAGTGTGTCCGTCAGCGTGATGAAGCAGGGAT
TCTGCTTACCCCGTCCCCCTTCGTCAAGCCGTCAATTATCCGAATAGTTACGGCTTATGA
CATCTTTGTGGACACATCATTCACTTTTTATTCACATCCGGCCCTGAACTCGCTAGGACT
TGCCCCGGTGCATTTTTTAAATACCCGCGAAAAATAGAGCTGATCGTCAAATCCAACATT
GCGCCCAACGGTCGCTATCGGCATTCGCGTAGTGCTAAGCAGAAGTTTCGCCTGGCTGAT
ACGCTGATCTTCGCGCCAGCTCAATACGCTAATGCCTAACTGCTGGCGGAACAGATGTGA
TAACCGGGAGGGCGACAGGCAGACATGCTGGGCGACGCTGGCGATATCAAAATGGCTGTC
CGCCAGATGGTCGCTGATATACTGGCAGGCATCGCGCACACGGCTATCCATCGGCGGGTG
CAACGACTCATTAATTACCGCCATACGTCTGAGCAACAACTGCTCCAGCAGATTGATCGC
CAGTAGCTCAGAATAGCGACCTTCCCCTTGCCCGGCGCTGATGATCTGCCCGAACAGTTC
GCTGAAATGCGGCTGGCGCGCCTCGTCCGGGCGGAAAAATCCTGTCTGGGCAAAGATTGT
CGGCCAGGTCAGCCACTCCTGCCAGTAGGCGCGAGGCCGGAAATAAACCCACTGGTGATA
CCACTCGCTGGCGTCCGGATGCCGTCCATAGTGATGAATCTCGCCCGGCGGAAACAATAA
TATATCGCCAGGCCGACAGACAAACTGCTCGCCATTATTATTAATGACGCCCTCTCCGCG
GATGGTCAGGTTAAGAATATATCCCTTCATGCCCAACGGACGATCGATAAAAAAATCCAG
ATATCCATTCGCTTCAATTGGCGTCAGCCCGGCGACCAGATGGGCATTAAATGAATATCC
CGGCAATAGCGGATCATTTTGCGTTTCAGCCATGATTTCTCTACCCCCCGATGTTCAGAG
AAGAAACAAATTGTCCATATCGACCAGGACGACAGAGCTTCCGTCTCCGCAAGACTTTGC
GCTTGATGAAAGCACGTATCAACCCCGCTTGTGAAAAGCGCTTTGTAACAAAAGCGTACA
GTTCAGGCGATAAAATTAAGTAACAGAAGTGTCTATAACTATGGCTGGAATGTCCACATT
GAATATTTGCACAGCGTCACACTTTGCAAAGCATTAGCATTTTTGTCCATAAGATTAGCG
GATCCTGCCTGACGGTTTTTGCCGCGACTCTCTACTGTTTCTCCATACCTGTTTTTCTGG
ATGGAGTAAGACGATGGCAATTGCAATTGGCCTCGATTTTGGCAGTGATTCAGTGCGCGC
TCTGGCAGTGGACTGCGCCACCGGCGACGAGATCGCCACCAGCGTAGAGTGGTATCCGCG
CTGGCAAGAAGGCCGTTATTGCGACGGCCCGAACAACCAGTTCCGTCATCATCCGCGCGA
CTACATGGAGTCAATGGAGGCGCGCTGAAAGCCGTTCTGGCACAATTAAGCGCCGCGCA
ACGCGCAAATGTCGTTGGCATTGGCGTTGACAGCACCGGCTCTACGCCAGCGCCGATTGA
CGCCGACGGTAACGTCCTGGCGCTGCGTCCAGAGTTCGCCGAGAACCCGAATGCGATGTT
TGTGCTGTGGAAAGATCACACCGCCGTGGAAGAGGCCGACGAAATCACTCGTCTGTGCCA
TAAGCCAGGCAAG

SEQ ID 2: p933
GTCGAGCTAGTAAAAGCATTTTAAATAAGGAGGAATAACACATATGAAAAAGATTTGGCT
GGCGCTGGCTGGTTTAGTTTTAGCGTTTAGCGCCATGGCAGGCGCAGATGACGTTGTTGA
CAGCAGCAAATCCTTCGTTATGGAAAACTTCTCCTCTTATCACGGCACCAAACCGGGCTA
TGTGGACAGCATTCAGAAAGGTATCCAAAAACCGAAATCTGGCACGCAGGGTAACTACGA
TGACGATTGGAAAGAATTCTACAGCACCGACAACAAATATGATGCGGCCGGTTACTCAGT
TGACAACGAAAATCCGCTGTCGGGCAAAGCCGGCGGTGTGGTTAAAGTCACGTATCCGGG
CCTGACCAAAGTCCTGGCCCTGAAAGTGGATAATGCAGAAACCATCAAAAAAGAACTGGG
```

-continued

```
TCTGAGCCTGACGGAACCGCTGATGGAACAGGTTGGCACCGAAGAATTTATCAAACGCTT
CGGCGATGGTGCCAGTCGTGTCGTGCTGTCCCTGCCGTTCGCAGAAGGTAGCTCTAGTGT
CGAATATATTAACAATTGGGAACAAGCGAAAGCCCTGTCCGTGGAACTGGAAATCAACTT
TGAAACCCGCGGCAAACGTGGTCAGGATGCGATGTATGAATACATGGCACAAGCTTGCGC
GGGTAATCGCGTTCGTCGCAGCGTCGGCTCCTCACTGTCTTGTATCAACCTGGACTGGGA
TGTTATCCGTGATAAAACCAAAACGAAAATCGAAAGTCTGAAAGAACACGGCCCGATCAA
AAACAAAATGAGCGAATCTCCGAATAAAACGGTGTCCGAAGAAAAAGCTAAACAGTATCT
GGAAGAATTCCACCAAACCGCACTGGAACATCCGGAACTGTCAGAACTGAAAACCGTCAC
GGGTACCAACCCGGTGTTTGCCGGCGCAAATTACGCAGCTTGGGCTGTGAACGTTGCGCA
AGTGATTGACTCGGAAACGGCCGATAATCTGGAAAAAACCACGCGGCCCTGAGTATTCT
GCCGGGCATCGGTTCCGTGATGGGTATTGCCGATGGCGCAGTTCATCACAACACCGAAGA
AATTGTCGCCCAGTCTATCGCACTGTCGAGCCTGATGGTTGCTCAAGCGATTCCGCTGGT
TGGCGAACTGGTTGATATCGGCTTTGCAGCTTACAACTTCGTGGAAAGTATCATCAACCT
GTTTCAGGTTGTCCATAACTCATATAATCGCCCGGCCTACTCGCCGGGTCACAAAACCCA
ACCGTTCCTGCATGACGGCTACGCGGTTAGCTGGAATACGGTCGAAGATTCTATTATCCG
TACCGGCTTTCAGGGTGAATCTGGCCACGACATTAAAATCACGGCTGAAAACACCCCGCT
GCCGATTGCCGGTGTTCTGCTGCCGACCATCCCGGGTAAACTGGATGTGAATAAATCAAA
AACCCATATCTCGGTTAACGGTCGCAAAATTCGTATGCGCTGCCGTGCGATCGACGGCGA
TGTGACCTTCTGTCGTCCGAAAAGCCCGGTCTATGTGGGCAACGGTGTTCATGCTAATCT
GCACGTCGCGTTTCATCGCTCTAGTTCCGAAAAAATCCACAGTAACGAAATCTCATCGGA
CTCCATTGGTGTGCTGGGCTACCAGAAAACGGTGGATCATACCAAAGTTAATAGCAAACT
GTCACTGTTCTTCGAAATCAAATCAGGCTCGCATCATCATCATCACCACTAATCTAGAGG
ATCCCCGGGTACCGAGCTCGAATTCTTGAAGACGAAAGGGCCTCGTGATACGCCTATTTT
TATAGGTTAATGTCATGATAATAATGGTTTCTTAGACGTCAGGTGGCACTTTTCGGGGAA
ATGTGCGCGGAACCCCTATTTGTTTATTTTTCTAAATACATTCAAATATGTATCCGCTCA
TGAGACAATAACCCTGATAAATGCTTCAATAATATTGAAAAAGGAAGAGTATGAGTATTC
AACATTTCCGTGTCGCCCTTATTCCCTTTTTTGCGGCATTTTGCCTTCCTGTTTTTGCTC
ACCCAGAAACGCTGGTGAAAGTAAAAGATGCTGAAGATCAGTTGGGTGCACGAGTGGGTT
ACATCGAACTGGATCTCAACAGCGGTAAGATCCTTGAGAGTTTTCGCCCCGAAGAACGTT
TTCCAATGATGAGCACTTTTAAAGTTCTGCTATGTGGCGCGGTATTATCCCGTGTTGACG
CCGGGCAAGAGCAACTCGGTCGCCGCATACACTATTCTCAGAATGACTTGGTTGAGTACT
CACCAGTCACAGAAAAGCATCTTACGGATGGCATGACAGTAAGAGAATTATGCAGTGCTG
CCATAACCATGAGTGATAACACTGCGGCCAACTTACTTCTGACAACGATCGGAGGACCGA
AGGAGCTAACCGCTTTTTTGCACAACATGGGGGATCATGTAACTCGCCTTGATCGTTGGG
AACCGGAGCTGAATGAAGCCATACCAAACGACGAGCGTGACACCACGATGCCTGCAGCAA
TGGCAACAACGTTGCGCAAACTATTAACTGGCGAACTACTTACTCTAGCTTCCCGGCAAC
AATTAATAGACTGGATGGAGGCGGATAAAGTTGCAGGACCACTTCTGCGCTCGGCCCTTC
CGGCTGGCTGGTTTATTGCTGATAAATCTGGAGCCGGTGAGCGTGGGTCTCGCGGTATCA
TTGCAGCACTGGGGCCAGATGGTAAGCCCTCCCGTATCGTAGTTATCTACACGACGGGGA
GTCAGGCAACTATGGATGAACGAAATAGACAGATCGCTGAGATAGGTGCCTCACTGATTA
AGCATTGGTAACTGTCAGACCAAGTTTACTCATATATACTTTAGATTGATTTAAAACTTC
```

-continued

```
ATTTTTAATTTAAAAGGATCTAGGTGAAGATCCTTTTTGATAATCTCATGACCAAAATCC

CTTAACGTGAGTTTTCGTTCCACTGAGCGTCAGACCCCGTAGAAAAGATCAAAGGATCTT

CTTGAGATCCTTTTTTTCTGCGCGTAATCTGCTGCTTGCAAACAAAAAAACCACCGCTAC

CAGCGGTGGTTTGTTTGCCGGATCAAGAGCTACCAACTCTTTTTCCGAAGGTAACTGGCT

TCAGCAGAGCGCAGATACCAAATACTGTCCTTCTAGTGTAGCCGTAGTTAGGCCACCACT

TCAAGAACTCTGTAGCACCGCCTACATACCTCGCTCTGCTAATCCTGTTACCAGTGGCTG

CTGCCAGTGGCGATAAGTCGTGTCTTACCGGGTTGGACTCAAGACGATAGTTACCGGATA

AGGCGCAGCGGTCGGGCTGAACGGGGGGTTCGTGCACACAGCCCAGCTTGGAGCGAACGA

CCTACACCGAACTGAGATACCTACAGCGTGAGCTATGAGAAAGCGCCACGCTTCCCGAAG

GGAGAAAGGCGGACAGGTATCCGGTAAGCGGCAGGGTCGGAACAGGAGAGCGCACGAGGG

AGCTTCCAGGGGGAAACGCCTGGTATCTTTATAGTCCTGTCGGGTTTCGCCACCTCTGAC

TTGAGCGTCGATTTTTGTGATGCTCGTCAGGGGGCGGAGCCTATGGAAAAACGCCAGCA

ACGCGGCCTTTTTACGGTTCCTGGCCTTTTGCTGGCCTTTTGCTCACATGTTCTTTCCTG

CGTTATCCCCTGATTCTGTGGATAACCGTATTACCGCCTTTGAGTGAGCTGATACCGCTC

GCCGCAGCCGAACGACCGAGCGCAGCGAGTCAGTGAGCGAGGAAGCGGAAGAGCGCCTGA

TGCGGTATTTTCTCCTTACGCATCTGTGCGGTATTTCACACCGCATGGTGCACTCTCAGT

ACAATCTGCTCTGATGCCGCATAGTTAAGCCAGTATACACTCCGCTATCGCTACGTGACT

GGGTCATGGCTGCGCCCCGACACCCGCCAACACCCGCTGACGCGCCCTGACGGGCTTGTC

TGCTCCCGGCATCCGCTTACAGACAAGCTGTGACCGTCTCCGGGAGCTGCATGTGTCAGA

GGTTTTCACCGTCATCACCGAAACGCGCGAGGCAGCTGCGGTAAAGCTCATCAGCGTGGT

CGTGAAGCGATTCACAGATGTCTGCCTGTTCATCCGCGTCCAGCTCGTTGAGTTTCTCCA

GAAGCGTTAATGTCTGGCTTCTGATAAAGCGGGCCATGTTAAGGGCGGTTTTTTCCTGTT

TGGTCACTGATGCCTCCGTGTAAGGGGATTTCTGTTCATGGGGGTAATGATACCGATGA

AACGAGAGAGGATGCTCACGATACGGGTTACTGATGATGAACATGCCCGGTTACTGGAAC

GTTGTGAGGGTAAACAACTGGCGGTATGGATGCGGCGGGACCAGAGAAAAATCACTCAGG

GTCAATGCCAGCGCTTCGTTAATACAGATGTAGGTGTTCCACAGGGTAGCCAGCAGCATC

CTGCGATGCAGATCCGGAACATAATGGTGCAGGGCGCTGACTTCCGCGTTTCCAGACTTT

ACGAAACACGGAAACCGAAGACCATTCATGTTGTTGCTCAGGTCGCAGACGTTTTGCAGC

AGCAGTCGCTTCACGTTCGCTCGCGTATCGGTGATTCATTCTGCTAACCAGTAAGGCAAC

CCCGCCAGCCTAGCCGGGTCCTCAACGACAGGAGCACGATCATGCGCACCCGTGGCCAGG

ACCCAACGCTGCCCGAGCGTCAACGGCGCCAGATACAGCAAACGGCTGCGGGGGAAATAC

GCGGTTAAACGATCGACTGCCGCTTTGCCGCTGCGCCACAGCCGCCAGCATAGCCAGCCT

CCGACCCACAGCAGCAACGCCGTCGCCAGCAGCAGCCATTTGAAATCTCCGCTCTGCATA

TCGGAAGGAATATCGATTGCCGCTCCCGCCAGAATGCCCGGCAGGAAATAAAACGGCGGC

CACAGCAAACAGCCAATCAAGTTCGGCCCAATAAATTTCGCCACGGGAAGATCCAGCATC

CCTGCCACCATCGGCACCAGCGGCCTCGTCGGACCGACAAAACGTCCGACCAGGATCGTG

AACATACTGTGCTGATGCAGCGCGTGTTCGGTTTATCCAGCAGCGACTTGTTCTTTTTC

ATAAAAGACCAGCGGTGTAGCGGCTTTTTAAAGCGCCACCCCAGCCAGAACGAAATCCAG

TCGCCCATCAGACAGCCGATAATACCCACCAGCCAGGCATGCCAAAAATTGAGCTCGCCG

CTGCCGATAAGCGCGCCCAGCCCCGCCATCAGTACCGTGCCGGGTAAAATCAACCCCACC
```

-continued

```
AGCGCCAGCGATTCCAGGAAGGCGACCAGCAACACGGCGATGAGCGAATACAGAGTGGAT

TGGGTGATAAAGTGTTCCAGCAGTGCTTGCATAGTGTGTCCGTCAGCGTGATGAAGCAGG

GATTCTGCTTACCCCGTCCCCCTTCGTCAAGCCGTCAATTATCCGAATAGTTACGGCTTA

TGACATCTTTGTGGACACATCATTCACTTTTTATTCACATCCGGCCCTGAACTCGCTAGG

ACTTGCCCCGGTGCATTTTTTAAATACCCGCGAAAAATAGAGCTGATCGTCAAATCCAAC

ATTGCGCCCAACGGTCGCTATCGGCATTCGCGTAGTGCTAAGCAGAAGTTTCGCCTGGCT

GATACGCTGATCTTCGCGCCAGCTCAATACGCTAATGCCTAACTGCTGGCGGAACAGATG

TGATAACCGGGAGGGCGACAGGCAGACATGCTGGGCGACGCTGGCGATATCAAAATGGCT

GTCCGCCAGATGGTCGCTGATATACTGGCAGGCATCGCGCACACGGCTATCCATCGGCGG

GTGCAACGACTCATTAATTACCGCCATACGTCTGAGCAACAACTGCTCCAGCAGATTGAT

CGCCAGTAGCTCAGAATAGCGACCTTCCCCTTGCCCGGCGCTGATGATCTGCCCGAACAG

TTCGCTGAAATGCGGCTGGCGCGCCTCGTCCGGGCGGAAAAATCCTGTCTGGGCAAAGAT

TGTCGGCCAGGTCAGCCACTCCTGCCAGTAGGCGCGAGGCCGGAAATAAACCCACTGGTG

ATACCACTCGCTGGCGTCCGGATGCCGTCCATAGTGATGAATCTCGCCCGGCGGAAACAA

TAATATATCGCCAGGCCGACAGACAAACTGCTCGCCATTATTATTAATGACGCCCTCTCC

GCGGATGGTCAGGTTAAGAATATATCCCTTCATGCCCAACGGACGATCGATAAAAAAATC

CAGATATCCATTCGCTTCAATTGGCGTCAGCCCGGCGACCAGATGGGCATTAAATGAATA

TCCCGGCAATAGCGGATCATTTTGCGTTTCAGCCATGATTTCTCTACCCCCGATGTTCA

GAGAAGAAACAAATTGTCCATATCGACCAGGACGACAGAGCTTCCGTCTCCGCAAGACTT

TGCGCTTGATGAAAGCACGTATCAACCCCGCTTGTGAAAAGCGCTTTGTAACAAAAGCGT

ACAGTTCAGGCGATAAAATTAAGTAACAGAAGTGTCTATAACTATGGCTGGAATGTCCAC

ATTGAATATTTGCACAGCGTCACACTTTGCAAAGCATTAGCATTTTTGTCCATAAGATTA

GCGGATCCTGCCTGACGGTTTTTGCCGCGACTCTCTACTGTTTCTCCATACCTGTTTTTC

TGGATGGAGTAAGACGATGGCAATTGCAATTGGCCTCGATTTTGGCAGTGATTCAGTGCG

CGCTCTGGCAGTGGACTGCGCCACCGGCGACGAGATCGCCACCAGCGTAGAGTGGTATCC

GCGCTGGCAAGAAGGCCGTTATTGCGACGGCCCGAACAACCAGTTCCGTCATCATCCGCG

CGACTACATGGAGTCAATGGAGGCCGCGCTGAAAGCCGTTCTGGCACAATTAAGCGCCGC

GCAACGCGCAAATGTCGTTGGCATTGGCGTTGACAGCACCGGCTCTACGCCAGCGCCGAT

TGACGCCGACGGTAACGTCCTGGCGCTGCGTCCAGAGTTCGCCGAGAACCCGAATGCGAT

GTTTGTGCTGTGGAAAGATCACACCGCCGTGGAAGAGGCCGACGAAATCACTCGTCTGTG

CCATAAGCCAGGCAAG
```

SEQ ID 3: Signal peptide containing Crm197 amino acid sequence
expressed from p932
```
MKKIWLALAGLVLAFSASAADDVVDSSKSFVMENFSSYHGTKPGYVDSIQKGIQKPKSGT

QGNYDDDWKEFYSTDNKYDAAGYSVDNENPLSGKAGGVVKVTYPGLTKVLALKVDNAETI

KKELGLSLTEPLMEQVGTEEFIKRFGDGASRVVLSLPFAEGSSSVEYINNWEQAKALSVE

LEINFETRGKRGQDAMYEYMAQACAGNRVRRSVGSSLSCINLDWDVIRDKTKTKIESLKE

HGPIKNKMSESPNKTVSEEKAKQYLEEFHQTALEHPELSELKTVTGTNPVFAGANYAAWA

VNVAQVIDSETADNLEKTTAALSILPGIGSVMGIADGAVHHNTEEIVAQSIALSSLMVAQ

AIPLVGELVDIGFAAYNFVESIINLFQVVHNSYNRPAYSPGHKTQPFLHDGYAVSWNTVE

DSIIRTGFQGESGHDIKITAENTPLPIAGVLLPTIPGKLDVNKSKTHISVNGRKIRMRCR
```

-continued

AIDGDVTFCRPKSPVYVGNGVHANLHVAFHRSSSEKIHSNEISSDSIGVLGYQKTVDHTK

VNSKLSLFFEIKSGSHHHHHH

SEQ ID 4: Signal peptide containing Crm197 amino acid sequence
expressed from p933
MKKIWLALAGLVLAFSAMAGADDVVDSSKSFVMENFSSYHGTKPGYVDSIQKGIQKPKSG

TQGNYDDDWKEFYSTDNKYDAAGYSVDNENPLSGKAGGVVKVTYPGLTKVLALKVDNAET

IKKELGLSLTEPLMEQVGTEEFIKRFGDGASRVVLSLPFAEGSSSVEYINNWEQAKALSV

ELEINFETRGKRGQDAMYEYMAQACAGNRVRRSVGSSLSCINLDWDVIRDKTKTKIESLK

EHGPIKNKMSESPNKTVSEEKAKQYLEEFHQTALEHPELSELKTVTGTNPVFAGANYAAW

AVNVAQVIDSETADNLEKTTAALSILPGIGSVMGIADGAVHHNTEEIVAQSIALSSLMVA

QAIPLVGELVDIGFAAYNFVESIINLFQVVHNSYNRPAYSPGHKTQPFLHDGYAVSWNTV

EDSIIRTGFQGESGHDIKITAENTPLPIAGVLLPTIPGKLDVNKSKTHISVNGRKIRMRC

RAIDGDVTFCRPKSPVYVGNGVHANLHVAFHRSSSEKIHSNEISSDSIGVLGYQKTVDHT

KVNSKLSLFFEIKSGSHHHHHH

SEQ ID 5: translated protein sequence of p722
MKKIWLALAGLVLAFSAMGADDVVDSSKSFVMENFSSYHGTKPGYVDSIQKGIQKPKSGT

QGNYDDDWKEFYSTDNKYDAAGYSVDNENPLSGKAGGVVKVTYPGLTKVLALKVDNAETI

KKELGLSLTEPLMEQVGTEEFIKRFGDGASRVVLSLPFAEGSSSVEYINNWEQAKALSVE

LEINFETRGKRGQDAMYEYMAQACAGNRVRRSVGSSLSCINLDWDVIRDKTKTKIESLKE

HGPIKNKMSESPNKTVSEEKAKQYLEEFHQTALEHPELSELKTVTGTNPVFAGANYAAWA

VNVAQVIDSETADNLEKTTAALSILPGIGSVMGIADGAVHHNTEEIVAQSIALSSLMVAQ

AIPLVGELVDIGFAAYNFVESIINLFQVVHNSYNRPAYSPGHKTQPFLHDGYAVSWNTVE

DSIIRTGFQGESGHDIKITAENTPLPIAGVLLPTIPGKLDVNKSKTHISVNGRKIRMRCR

AIDGDVTFCRPKSPVYVGNGVHANLHVAFHRSSSEKIHSNEISSDSIGVLGYQKTVDHTK

VNSKLSLFFEIKSGSHHHHHH

SEQ ID 6: mature, secreted CRM197
GADDVVDSSKSFVMENFSSYHGTKPGYVDSIQKGIQKPKSGTQGNYDDDWKEFYSTDNKY

DAAGYSVDNENPLSGKAGGVVKVTYPGLTKVLALKVDNAETIKKELGLSLTEPLMEQVGT

EEFIKRFGDGASRVVLSLPFAEGSSSVEYINNWEQAKALSVELEINFETRGKRGQDAMYE

YMAQACAGNRVRRSVGSSLSCINLDWDVIRDKTKTKIESLKEHGPIKNKMSESPNKTVSE

EKAKQYLEEFHQTALEHPELSELKTVTGTNPVFAGANYAAWAVNVAQVIDSETADNLEKT

TAALSILPGIGSVMGIADGAVHHNTEEIVAQSIALSSLMVAQAIPLVGELVDIGFAAYNF

VESIINLFQVVHNSYNRPAYSPGHKTQPFLHDGYAVSWNTVEDSIIRTGFQGESGHDIKI

TAENTPLPIAGVLLPTIPGKLDVNKSKTHISVNGRKIRMRCRAIDGDVTFCRPKSPVYVG

NGVHANLHVAFHRSSSEKIHSNEISSDSIGVLGYQKTVDHTKVNSKLSLFFEIKS

What is claimed is:

1. A method of producing CRM197 comprising the steps:

(a) culturing at 18-37 degrees C.° a *E. coli* cell comprising an expression plasmid containing a nucleic acid encoding CRM197 operatively linked to a promoter;

wherein the nucleic acid encoding CRM197 is fused to a nucleic acid encoding a heterologous signal peptide that targets CRM197 to the periplasm of the *E. coli* cell;

wherein the nucleic acid encoding a heterologous signal peptide encodes a cleavage site between the signal peptide that targets CRM197 to the periplasm and the CRM197 protein;

wherein the cleavage site sequence comprises the amino acid sequence aa1-aa2-aa3-(cleavage site)-aa4-aa5-aa6-aa7;

wherein (A) wherein the cleavage site sequence comprises the amino acid sequence aa1-aa2-aa3-(cleavage site)-aa4-aa5-aa6-aa7; and (B) wherein aa4 to aa7 is selected from ala-asp-asp-val (SEQ ID NO: 7) and ala-gly-ala-asp (SEQ ID NO: 10) and met-gly-ala-asp (SEQ ID NO: 11); and (b) inducing expression of CRM197 at a culture density of OD600>0.3 at a temperature of 18-37 degrees C.°.

2. The method of claim 1 wherein the wild type signal peptide of CRM197 has been deleted.

3. The method of claim 1 wherein the wild type signal peptide of CRM197 has been replaced by the heterologous signal peptide.

4. The method of claim 1 wherein the heterologous signal peptide is selected from the group consisting of the signal peptide from *E. coli* outer membrane porin (OmpA), *E. coli* maltose binding protein (MalE), *E. coli* DsbA, *E. carotovorans* pectate lyase (PelB), and *Bacillus* sp. endoxylanase (XynA).

5. The method of claim 1 wherein CRM197 is produced at a concentration of at least 10, at least 25, at least 50, at least 75, at least 100, at least 125, at least 150, at least 175, at least 200, at least 225, at least 250, at least 300, at least 400, at least 500, at least 600, at least 700, at least 800, at least 900, or at least 1000 mg protein per liter culture medium.

6. The method of claim 1 wherein at least 50% of the produced protein is properly folded as determined by circular dichroism.

7. The method of claim 1 wherein at least 50% of the produced protein is not present in aggregates.

8. The method of claim 1 wherein at least 50% of the produced protein is soluble.

9. The method of claim 1 wherein the high copy expression plasmid encodes the sequence of SEQ ID NO: 3 or 5.

10. The method of claim 1 wherein the nucleic acid encoding a heterologous signal peptide is operatively linked to a promoter selected from the group consisting of the 1-arabinose inducible araBAD promoter (PBAD), the lac promoter, the 1-rhamnose inducible rhaP BAD promoter, the T7 RNA polymerase promoter, the trc and tac promoter, the lambda phage promoter p L, and the anhydrotetracycline-inducible tetA promoter/operator.

11. The method of claim 1 wherein the high copy expression plasmid is selected from the group consisting of: pEC415, pBR322, pBAD, pET series, pUC series, pACT3, pEXT22, pEXT20, pBLUESCRIPT series, and pGEM series.

12. The method of claim 1 wherein the expression of CRM197 is induced at a culture density of OD600>1.

13. The method of claim 1 wherein CRM197 is expressed at a temperature of 20, 25, 30, 32, 35° C. or 37° C.

14. The method of claim 1 wherein at least 50% of the expressed CRM197 have an N-terminus of ADDV (SEQ ID NO: 7) or MGADDV (SEQ ID NO: 12).

15. The method of claim 1 wherein at least 50% of the expressed CRM197 have a disulfide bond between Cys186 and Cys201 (SEQ ID NO: 6).

16. The method of claim 5 wherein at least 50% of the produced protein is properly folded as determined by circular dichroism.

17. The method of claim 5 wherein at least 50% of the produced protein is not present in aggregates.

18. The method of claim 5 wherein at least 50% of the produced protein is soluble.

19. The method of claim 5 wherein the high copy expression plasmid encodes the sequence of SEQ ID NO: 3 or 5.

20. The method of claim 5 wherein the nucleic acid encoding a heterologous signal peptide is operatively linked to a promoter selected from the group consisting of the 1-arabinose inducible araBAD promoter (PBAD), the lac promoter, the 1-rhamnose inducible rhaP BAD promoter, the T7 RNA polymerase promoter, the trc and tac promoter, the lambda phage promoter p L, and the anhydrotetracycline-inducible tetA promoter/operator.

21. The method of claim 5 wherein the high copy expression plasmid is selected from the group consisting of: pEC415, pBR322, pBAD, pET series, pUC series, pACT3, pEXT22, pEXT20, pBLUESCRIPT series, and pGEM series.

22. The method of claim 5 wherein the expression of CRM197 is induced at a culture density of OD600>1.

23. The method of claim 5 wherein CRM197 is expressed at a temperature of 20, 25, 30, 32, 35° C. or 37° C.

24. The method of claim 5 wherein at least 50% of the expressed CRM197 have an N-terminus of ADDV (SEQ ID NO: 7) or MGADDV (SEQ ID NO: 12).

25. The method of claim 5 wherein at least 50% of the expressed CRM197 have a disulfide bond between Cys186 and Cys201 (SEQ ID NO: 6).

26. The method of claim 1, wherein (A) aa1 is selected from Ala, Ser, Gly, Cys, Thr, and Gln;

(B) aa2 is selected from any natural amino acid; and (C) aa3 is selected from any natural amino acid except Phe, His, Tyr, Trp, Asp, Glu, Lys, Arg, Asn, and Gln.

27. The method of claim 1, wherein (A) aa1 is selected from Ala, Ser, Gly, Cys, Thr, and Gln;

(B) aa2 is Met; and (C) aa3 is selected from any natural amino acid except Phe, His, Tyr, Trp, Asp, Glu, Lys, Arg, Asn, and Gln.

* * * * *

SEQUENCE LISTING

<160> NUMBER OF SEQ ID NOS: 34

<210> SEQ ID NO 1
<211> LENGTH: 7093
<212> TYPE: DNA
<213> ORGANISM: Artificial Sequence
<220> FEATURE:
<223> OTHER INFORMATION: expression plasmid p932

<400> SEQUENCE: 1

```
gtcgagctag taaaagcatt ttaaataagg aggaataaca catatgaaaa agatttggct      60
ggcgctggct ggtttagttt tagcgtttag cgccagcgcc gcagatgacg ttgttgacag     120
cagcaaatcc ttcgttatgg aaaacttctc ctcttatcac ggcaccaaac cgggctatgt     180
ggacagcatt cagaaaggta tccaaaaacc gaaatctggc acgcagggta actacgatga     240
cgattggaaa gaattctaca gcaccgacaa caaatatgat gcggccggtt actcagttga     300
caacgaaaat ccgctgtcgg gcaaagccgg cggtgtggtt aaagtcacgt atccgggcct     360
gaccaaagtc ctggccctga agtggataa tgcagaaacc atcaaaaaag aactgggtct     420
gagcctgacg gaaccgctga tggaacaggt tggcaccgaa gaatttatca aacgcttcgg     480
cgatggtgcc agtcgtgtcg tgctgtccct gccgttcgca gaaggtagct ctagtgtcga     540
atatattaac aattgggaac aagcgaaagc cctgtccgtg gaactggaaa tcaactttga     600
aacccgcggc aaacgtggtc aggatgcgat gtatgaatac atggcacaag cttgcgcggg     660
taatcgcgtt cgtcgcagcg tcggctcctc actgtcttgt atcaacctgg actggatgt      720
tatccgtgat aaaaccaaaa cgaaaatcga agtctgaaa gaacacggcc cgatcaaaaa     780
caaaatgagc gaatctccga ataaaacggt gtccgaagaa aaagctaaac agtatctgga     840
agaattccac caaaccgcac tggaacatcc ggaactgtca gaactgaaaa ccgtcacggg     900
taccaacccg gtgtttgccg cgcaaatta cgcagcttgg gctgtgaacg ttgcgcaagt     960
gattgactcg gaaacggccg ataatctgga aaaaaccacg gcggccctga gtattctgcc    1020
gggcatcggt tccgtgatgg gtattgccga tggcgcagtt catcacaaca ccgaagaaat    1080
tgtcgcccag tctatcgcac tgtcgagcct gatggttgct caagcgattc cgctggttgg    1140
cgaactggtt gatatcggct ttgcagctta caacttcgtg gaaagtatca tcaacctgtt    1200
tcaggttgtc cataactcat ataatcgccc ggcctactcg ccgggtcaca aaacccaacc    1260
gttcctgcat gacggctacg cggttagctg gaatacggtc gaagattcta ttatccgtac    1320
cggcttttcag ggtgaatctg gccacgacat taaaatcacg gctgaaaaca ccccgctgcc    1380
gattgccggt gttctgctgc cgaccatccc gggtaaactg gatgtgaata atcaaaaaac    1440
ccatatctcg gttaacggtc gcaaaattcg tatgcgctgc cgtgcgatcg acggcgatgt    1500
gaccttctgt cgtccgaaaa gcccggtcta tgtgggcaac ggtgttcatg ctaatctgca    1560
cgtcgcgttt catcgctcta gttccgaaaa aatccacagt aacgaaatct catcggactc    1620
cattggtgtg ctgggctacc agaaaacggt ggatcatacc aaagttaata gcaaactgtc    1680
actgttcttc gaaatcaaat caggctcgca tcatcatcat caccactaat ctagaggatc    1740
cccgggtacc gagctcgaat tcttgaagac gaaagggcct cgtgatacgc ctatttttat    1800
aggttaatgt catgataata atggtttctt agacgtcagg tggcacttttt cggggaaatg    1860
tgcgcggaac ccctatttgt ttatttttct aaatacattc aaatatgtat ccgctcatga    1920
gacaataacc ctgataaatg cttcaataat attgaaaaag gaagagtatg agtattcaac    1980
atttccgtgt cgcccttatt ccctttttg cggcattttg ccttcctgtt tttgctcacc    2040
cagaaacgct ggtgaaagta aaagatgctg aagatcagtt gggtgcacga gtgggttaca    2100
tcgaactgga tctcaacagc ggtaagatcc ttgagagttt tcgccccgaa gaacgttttc    2160
caatgatgag cacttttaaa gttctgctat gtggcgcggt attatcccgt gttgacgccg    2220
ggcaagagca actcggtcgc cgcatacact attctcagaa tgacttggtt gagtactcac    2280
```

```
cagtcacaga aaagcatctt acggatggca tgacagtaag agaattatgc agtgctgcca      2340
taaccatgag tgataacact gcggccaact tacttctgac aacgatcgga ggaccgaagg      2400
agctaaccgc ttttttgcac aacatggggg atcatgtaac tcgccttgat cgttgggaac      2460
cggagctgaa tgaagccata ccaaacgacg agcgtgacac cacgatgcct gcagcaatgg      2520
caacaacgtt gcgcaaacta ttaactggcg aactacttac tctagcttcc cggcaacaat      2580
taatagactg gatggaggcg gataaagttg caggaccact tctgcgctcg gcccttccgg      2640
ctggctggtt tattgctgat aaatctggag ccggtgagcg tgggtctcgc ggtatcattg      2700
cagcactggg gccagatggt aagccctccc gtatcgtagt tatctacacg acggggagtc      2760
aggcaactat ggatgaacga atagacaga tcgctgagat aggtgcctca ctgattaagc      2820
attggtaact gtcagaccaa gtttactcat atatacttta gattgattta aaacttcatt      2880
tttaatttaa aaggatctag gtgaagatcc tttttgataa tctcatgacc aaaatccctt      2940
aacgtgagtt ttcgttccac tgagcgtcag accccgtaga aaagatcaaa ggatcttctt      3000
gagatccttt ttttctgcgc gtaatctgct gcttgcaaac aaaaaaacca ccgctaccag      3060
cggtggtttg tttgccggat caagagctac caactctttt tccgaaggta actggcttca      3120
gcagagcgca gataccaaat actgtccttc tagtgtagcc gtagttaggc caccacttca      3180
agaactctgt agcaccgcct acatacctcg ctctgctaat cctgttacca gtggctgctg      3240
ccagtggcga taagtcgtgt cttaccgggt tggactcaag acgatagtta ccggataagg      3300
cgcagcggtc gggctgaacg gggggttcgt gcacacagcc cagcttggag cgaacgacct      3360
acaccgaact gagatacccta cagcgtgagc tatgagaaag cgccacgctt cccgaaggga      3420
gaaaggcgga caggtatccg gtaagcggca gggtcggaac aggagagcgc acgagggagc      3480
ttccaggggg aaacgcctgg tatctttata gtcctgtcgg gtttcgccac ctctgacttg      3540
agcgtcgatt tttgtgatgc tcgtcagggg ggcggagcct atggaaaaac gccagcaacg      3600
cggccttttt acggttcctg gccttttgct ggccttttgc tcacatgttc tttcctgcgt      3660
tatcccctga ttctgtggat aaccgtatta ccgcctttga gtgagctgat accgctcgcc      3720
gcagccgaac gaccgagcgc agcgagtcag tgagcgagga agcggaagag cgcctgatgc      3780
ggtattttct ccttacgcat ctgtgcggta tttcacaccg catggtgcac tctcagtaca      3840
atctgctctg atgccgcata gttaagccag tatacactcc gctatcgcta cgtgactggg      3900
tcatggctgc gccccgacac ccgccaacac ccgctgacgc gccctgacgg gcttgtctgc      3960
tcccggcatc cgcttacaga caagctgtga ccgtctccgg gagctgcatg tgtcagaggt      4020
tttcaccgtc atcaccgaaa cgcgcgaggc agctgcggta agctcatca gcgtggtcgt      4080 gaagcgattc acagatgtct gcctgttcat ccgcgtccag ctcgttgagt ttctccagaa      4140
gcgttaatgt ctggcttctg ataaagcggg ccatgttaag gcggtttttt cctgtttgg       4200 tcactgatgc ctccgtgtaa gggggatttc tgttcatggg ggtaatgata ccgatgaaac      4260
gagagaggat gctcacgata cgggttactg atgatgaaca tgcccggtta ctggaacgtt      4320
gtgagggtaa acaactggcg gtatggatgc ggcgggacca gagaaaaatc actcagggtc      4380
aatgccagcg cttcgttaat acagatgtag gtgttccaca gggtagccag cagcatcctg      4440
cgatgcagat ccggaacata atggtgcagg gcgctgactt ccgcgtttcc agactttacg      4500
aaacacggaa accgaagacc attcatgttg ttgctcaggt cgcagacgtt ttgcagcagc      4560
agtcgcttca cgttcgctcg cgtatcgtg attcattctg ctaaccagta aggcaacccc      4620
gccagcctag ccgggtcctc aacgacagga gcacgatcat gcgcacccgt ggccaggacc      4680
```

-continued

```
caacgctgcc cgagcgtcaa cggcgccaga tacagcaaac ggctgcgggg gaaatacgcg   4740
gttaaacgat cgactgccgc tttgccgctg cgccacagcc gccagcatag ccagcctccg   4800
acccacagca gcaacgccgt cgccagcagc agccatttga atctccgct ctgcatatcg    4860 gaaggaatat cgattgccgc tcccgccaga atgcccggca ggaaataaaa cggcggccac   4920
agcaaacagc caatcaagtt cggcccaata aatttcgcca cgggaagatc cagcatccct   4980
gccaccatcg gcaccagcgg cctcgtcgga ccgacaaaac gtccgaccag gatcgtgaac   5040
atactgtgct gatgcagcgc gtgttcggtt ttatccagca gcgacttgtt cttttcata    5100 aaagaccagc ggtgtagcgg cttttaaag cgcaccccca gccagaacga aatccagtcg    5160
cccatcagac agccgataat acccaccagc caggcatgcc aaaaattgag ctcgccgctg   5220
ccgataagcg cgcccagccc cgccatcagt accgtgccgg gtaaaatcaa ccccaccagc   5280
gccagcgatt ccaggaaggc gaccagcaac acggcgatga gcgaatacag agtggattgg   5340
gtgataaagt gttccagcag tgcttgcata gtgtgtccgt cagcgtgatg aagcagggat   5400
tctgcttacc ccgtcccct cgtcaagcc gtcaattatc cgaatagtta cggcttatga    5460
catctttgtg gacacatcat tcactttta ttcacatccg gccctgaact cgctaggact    5520
tgccccggtg catttttaa atacccgcga aaatagagc tgatcgtcaa atccaacatt     5580
gcgcccaacg tcgctatcg gcattcgcgt agtgctaagc agaagtttcg cctggctgat    5640
acgctgatct tcgcgccagc tcaatacgct aatgcctaac tgctggcgga acagatgtga   5700
taaccgggag ggcgacaggc agacatgctg ggcgacgctg gcgatatcaa aatggctgtc   5760
cgccagatgg tcgctgatat actggcaggc atcgcgcaca cggctatcca tcggcgggtg   5820
caacgactca ttaattaccg ccatacgtct gagcaacaac tgctccagca gattgatcgc   5880
cagtagctca gaatagcgac cttccccttg cccggcgctg atgatctgcc cgaacagttc   5940
gctgaaatgc ggctggcgcg cctcgtccgg gcggaaaaat cctgtctggg caaagattgt   6000
cggccaggtc agccactcct gccagtaggc gcgaggccgg aaataaaccc actggtgata   6060
ccactcgctg gcgtccggat gccgtccata gtgatgaatc tcgcccggcg gaaacaataa   6120
tatatcgcca ggccgacaga caaactgctc gccattatta ttaatgacgc cctctccgcg   6180
gatggtcagg ttaagaatat atcccttcat gcccaacgga cgatcgataa aaaaatccag   6240
atatccattc gcttcaattg gcgtcagccc ggcgaccaga tgggcattaa atgaatatcc   6300
cggcaatagc ggatcatttt gcgtttcagc catgatttct ctaccccccg atgttcagag   6360
aagaaacaaa ttgtccatat cgaccaggac gacagagctt ccgtctccgc aagactttgc   6420
gcttgatgaa agcacgtatc aaccccgctt gtgaaaagcg ctttgtaaca aaagcgtaca   6480
gttcaggcga taaaattaag taacagaagt gtctataact atggctggaa tgtccacatt   6540
gaatatttgc acagcgtcac actttgcaaa gcattagcat ttttgtccat aagattagcg   6600
gatcctgcct gacggttttt gccgcgactc tctactgttt ctccatacct gtttttctgg   6660
atggagtaag acgatggcaa ttgcaattgg cctcgatttt ggcagtgatt cagtgcgcgc   6720
tctggcagtg gactgcgcca ccggcgacga gatcgccacc agcgtagagt ggtatccgcg   6780
ctggcaagaa ggccgttatt gcgacggccc gaacaaccag ttccgtcatc atccgcgcga   6840
ctacatggag tcaatggagg ccgcgctgaa agccgttctg gcacaattaa gcgccgcgca   6900
acgcgcaaat gtcgttggca ttggcgttga cagcaccggc tctacgccag cgccgattga   6960
cgccgacggt aacgtcctgg cgctgcgtcc agagttcgcc gagaacccga atgcgatgtt   7020
```

| | | |
|---|---|---|
| tgtgctgtgg aaagatcaca ccgccgtgga agaggccgac gaaatcactc gtctgtgcca | 7080 | |
| taagccaggc aag | 7093 | |

<210> SEQ ID NO 2
<211> LENGTH: 7096
<212> TYPE: DNA
<213> ORGANISM: Artificial Sequence
<220> FEATURE:
<223> OTHER INFORMATION: expression plasmid p933

<400> SEQUENCE: 2

| | |
|---|---|
| gtcgagctag taaaagcatt ttaaataagg aggaataaca catatgaaaa agatttggct | 60 |
| ggcgctggct ggtttagttt tagcgtttag cgccatggca ggcgcagatg acgttgttga | 120 |
| cagcagcaaa tccttcgtta tggaaaactt ctcctcttat cacggcacca aaccgggcta | 180 |
| tgtggacagc attcagaaag gtatccaaaa accgaaatct ggcacgcagg gtaactacga | 240 |
| tgacgattgg aaagaattct acagcaccga caacaaatat gatgcggccg gttactcagt | 300 |
| tgacaacgaa atccgctgt cgggcaaagc cggcggtgtg gttaaagtca cgtatccggg | 360 |
| cctgaccaaa gtcctggccc tgaaagtgga taatgcagaa accatcaaaa agaactggg | 420 |
| tctgagcctg acgaaccgc tgatggaaca ggttggcacc gaagaattta tcaaacgctt | 480 |
| cggcgatggt gccagtcgtg tcgtgctgtc cctgccgttc gcagaaggta gctctagtgt | 540 |
| cgaatatatt aacaattggg aacaagcgaa agccctgtcc gtggaactgg aaatcaactt | 600 |
| tgaaacccgc ggcaaacgtg gtcaggatgc gatgtatgaa tacatggcac aagcttgcgc | 660 |
| gggtaatcgc gttcgtcgca gcgtcggctc ctcactgtct tgtatcaacc tggactggga | 720 |
| tgttatccgt gataaaacca aaacgaaaat cgaaagtctg aaagaacacg gcccgatcaa | 780 |
| aaacaaaatg agcgaatctc cgaataaaac ggtgtccgaa gaaaaagcta acagtatct | 840 |
| ggaagaattc caccaaaccg cactggaaca tccggaactg tcagaactga aaccgtcac | 900 |
| gggtaccaac ccggtgtttg ccggcgcaaa ttacgcagct tgggctgtga cgttgcgca | 960 |
| agtgattgac tcggaaacgg ccgataatct ggaaaaaacc acggcggccc tgagtattct | 1020 |
| gccgggcatc ggttccgtga tgggtattgc cgatggcgca gttcatcaca caccgaaga | 1080 |
| aattgtcgcc cagtctatcg cactgtcgag cctgatggtt gctcaagcga ttccgctggt | 1140 |
| tggcgaactg gttgatatcg ctttgcagc ttacaacttc gtggaaagta tcatcaacct | 1200 |
| gtttcaggtt gtccataact catataatcg cccggcctac tcgccgggtc acaaaaccca | 1260 |
| accgttcctg catgacggct acgcggttag ctggaatacg gtcgaagatt ctattatccg | 1320 |
| taccggcttt cagggtgaat ctggccacga cattaaaatc acggctgaaa acaccccgct | 1380 |
| gccgattgcc ggtgttctgc tgccgaccat cccgggtaaa ctggatgtga ataaatcaaa | 1440 |
| aacccatatc tcggttaacg gtcgcaaaat tcgtatgcgc tgccgtgcga tcgacggcga | 1500 |
| tgtgaccttc gtcgtccga aaagcccggt ctatgtgggc aacggtgttc atgctaatct | 1560 |
| gcacgtcgcg tttcatcgct ctagttccga aaaaatccac agtaacgaaa tctcatcgga | 1620 |
| ctccattggt gtgctgggct accagaaaac ggtggatcat ccaaagtta atagcaaact | 1680 |
| gtcactgttc ttcgaaatca atcaggctc gcatcatcat catcaccact aatctagagg | 1740 |
| atccccgggt accgagctcg aattcttgaa gacgaaaggg cctcgtgata cgcctatttt | 1800 |
| tataggttaa tgtcatgata ataatggttt cttagacgtc aggtggcact tttcggggaa | 1860 |
| atgtgcgcg aaccccctatt tgtttatttt tctaaataca ttcaaatatg tatccgctca | 1920 |
| tgagacaata accctgataa atgcttcaat aatattgaaa aggaagagt atgagtattc | 1980 |

```
aacatttccg tgtcgccctt attccctttt ttgcggcatt ttgccttcct gttttttgctc   2040 acccagaaac gctggtgaaa gtaaaagatg ctgaagatca gttgggtgca cgagtgggtt   2100
acatcgaact ggatctcaac agcggtaaga tccttgagag ttttcgcccc gaagaacgtt   2160
ttccaatgat gagcactttt aaagttctgc tatgtggcgc ggtattatcc cgtgttgacg   2220
ccgggcaaga gcaactcggt cgccgcatac actattctca gaatgacttg gttgagtact   2280
caccagtcac agaaaagcat cttacggatg gcatgacagt aagagaatta tgcagtgctg   2340
ccataaccat gagtgataac actgcggcca acttacttct gacaacgatc ggaggaccga   2400
aggagctaac cgcttttttg cacaacatgg ggatcatgt aactcgcctt gatcgttggg   2460
aaccggagct gaatgaagcc ataccaaacg acgagcgtga caccacgatg cctgcagcaa   2520
tggcaacaac gttgcgcaaa ctattaactg gcgaactact tactctagct tcccggcaac   2580
aattaataga ctggatggag gcggataaag ttgcaggacc acttctgcgc tcggcccttc   2640
cggctggctg gtttattgct gataaatctg gagccgtga gcgtgggtct cgcggtatca   2700
ttgcagcact ggggccagat ggtaagccct cccgtatcgt agttatctac acgacgggga   2760
gtcaggcaac tatggatgaa cgaaatagac agatcgctga gataggtgcc tcactgatta   2820
agcattggta actgtcagac caagtttact catatatact ttagattgat ttaaaacttc   2880 attttttaatt taaaggatc taggtgaaga tcctttttga taatctcatg accaaaatcc   2940
cttaacgtga gttttcgttc cactgagcgt cagacccgt agaaaagatc aaggatctt   3000 cttgagatcc ttttttctg cgcgtaatct gctgcttgca acaaaaaaa ccaccgctac   3060 cagcggtggt ttgtttgccg gatcaagagc taccaactct ttttccgaag gtaactggct   3120
tcagcagagc gcagatacca atactgtcc ttctagtgta gccgtagtta ggccaccact   3180
tcaagaactc tgtagcaccg cctacatacc tcgctctgct aatcctgtta ccagtggctg   3240
ctgccagtgg cgataagtcg tgtcttaccg ggttggactc aagacgatag ttaccggata   3300
aggcgcagcg gtcgggctga acggggggtt cgtgcacaca gcccagcttg gagcgaacga   3360
cctacaccga actgagatac ctacagcgtg agctatgaga aagcgccacg cttcccgaag   3420
ggagaaaggc ggacaggtat ccggtaagcg gcagggtcgg aacaggagag cgcacgaggg   3480
agcttccagg gggaaacgcc tggtatcttt atagtcctgt cgggtttcgc cacctctgac   3540
ttgagcgtcg attttgtga tgctcgtcag ggggcggag cctatggaaa aacgccagca   3600
acgcggcctt tttacggttc ctggcctttt gctggccttt tgctcacatg ttctttcctg   3660
cgttatcccc tgattctgtg gataaccgta ttaccgcctt tgagtgagct gataccgctc   3720
gccgcagccg aacgaccgag cgcagcgagt cagtgagcga ggaagcggaa gagcgcctga   3780
tgcggtattt tctccttacg catctgtgcg gtatttcaca ccgcatggtg cactctcagt   3840
acaatctgct ctgatgccgc atagttaagc cagtatacac tccgctatcg ctacgtgact   3900
gggtcatggc tgcgccccga cacccgccaa cacccgctga cgcgccctga cgggcttgtc   3960
tgctcccggc atccgcttac agacaagctg tgaccgtctc cgggagctgc atgtgtcaga   4020
ggttttcacc gtcatcaccg aaacgcgcga ggcagctgcg gtaaagctca tcagcgtggt   4080
cgtgaagcga ttcacagatg tctgcctgtt catccgcgtc cagctcgttg agtttctcca   4140
gaagcgttaa tgtctggctt ctgataaagc gggccatgtt aagggcggtt ttttcctgtt   4200
tggtcactga tgcctccgtg taaggggat ttctgttcat gggggtaatg ataccgatga   4260
aacgagagag gatgctcacg atacgggtta ctgatgatga acatgcccgg ttactggaac   4320
```

```
gttgtgaggg taaacaactg gcggtatgga tgcggcggga ccagagaaaa atcactcagg    4380
gtcaatgcca gcgcttcgtt aatacagatg taggtgttcc acagggtagc cagcagcatc    4440
ctgcgatgca gatccggaac ataatggtgc agggcgctga cttccgcgtt tccagacttt    4500
acgaaacacg gaaaccgaag accattcatg ttgttgctca ggtcgcagac gttttgcagc    4560
agcagtcgct tcacgttcgc tcgcgtatcg gtgattcatt ctgctaacca gtaaggcaac    4620
cccgccagcc tagccgggtc ctcaacgaca ggagcacgat catgcgcacc cgtgccagg     4680 acccaacgct gcccgagcgt caacggcgcc agatacagca aacggctgcg ggggaaatac    4740
gcggttaaac gatcgactgc cgcttttgccg ctgcgccaca gccgccagca tagccagcct   4800
ccgacccaca gcagcaacgc cgtcgccagc agcagccatt tgaaatctcc gctctgcata    4860
tcggaaggaa tatcgattgc cgctcccgcc agaatgcccg gcaggaaata aaacggcggc    4920
cacagcaaac agccaatcaa gttcggccca ataaatttcg ccacgggaag atccagcatc    4980
cctgccacca tcggcaccag cggcctcgtc ggaccgacaa aacgtccgac caggatcgtg    5040
aacatactgt gctgatgcag cgcgtgttcg gttttatcca gcagcgactt gttcttttc     5100 ataaaagacc agcggtgtag cggctttta aagcgccacc ccagccagaa cgaaatccag     5160
tcgcccatca gacagccgat aatacccacc agccaggcat gccaaaaatt gagctcgccg    5220
ctgccgataa gcgcgcccag ccccgccatc agtaccgtgc cgggtaaaat caaccccacc    5280
agcgccagcg attccaggaa ggcgaccagc aacacggcga tgagcgaata cagagtggat    5340
tgggtgataa agtgttccag cagtgcttgc atagtgtgtc cgtcagcgtg atgaagcagg    5400
gattctgctt accccgtccc ccttcgtcaa gccgtcaatt atccgaatag ttacggctta    5460
tgacatcttt gtggacacat cattcacttt ttattcacat ccggccctga actcgctagg    5520
acttgccccg gtgcattttt taaatacccg cgaaaaatag agctgatcgt caaatccaac    5580
attgcgccca acgtcgctca tcggcattcg cgtagtgcta agcagaagtt tcgcctggct    5640
gatacgctga tcttcgcgcc agctcaatac gctaatgcct aactgctggc ggaacagatg    5700
tgataaccgg gagggcgaca ggcagacatg ctgggcgacg ctggcgatat caaaatggct    5760
gtccgccaga tggtcgctga tatactggca ggcatcgcgc acacggctat ccatcggcgg    5820
gtgcaacgac tcattaatta ccgccatacg tctgagcaac aactgctcca gcagattgat    5880
cgccagtagc tcagaatagc gaccttcccc ttgcccggcg ctgatgatct gcccgaacag    5940
ttcgctgaaa tgcggctggc gcgcctcgtc cgggcggaaa atcctgtctt gggcaaagat    6000
tgtcggccag gtcagccact cctgccagta ggcgcgaggc cggaaataaa cccactggtg    6060
ataccactcg ctggcgtccg gatgccgtcc atagtgatga atctcgcccg gcggaaacaa    6120
taatatatcg ccaggccgac agacaaactg ctcgccatta ttattaatga cgccctctcc    6180
gcggatggtc aggttaagaa tatatccctt catgcccaac ggacgatcga taaaaaaatc    6240
cagatatcca ttcgcttcaa ttggcgtcag cccggcgacc agatgggcat taaatgaata    6300
tcccggcaat agcggatcat tttgcgtttc agccatgatt tctctacccc ccgatgttca    6360
gagaagaaac aaattgtcca tatcgaccag gacgacagag cttccgtctc cgcaagactt    6420
tgcgcttgat gaaagcacgt atcaaccccg cttgtgaaaa gcgctttgta acaaaagcgt    6480
acagttcagg cgataaaatt aagtaacaga agtgtctata actatggctg gaatgtccac    6540
attgaatatt tgcacagcgt cacactttgc aaagcattag cattttttgtc cataagatta    6600 gcggatcctg cctgacggtt tttgccgcga ctctctactg tttctccata cctgtttttc    6660
tggatggagt aagacgatgg caattgcaat tggcctcgat tttggcagtg attcagtgcg    6720
```

-continued

```
cgctctggca gtggactgcg ccaccggcga cgagatcgcc accagcgtag agtggtatcc    6780
gcgctggcaa gaaggccgtt attgcgacgg cccgaacaac cagttccgtc atcatccgcg    6840
cgactacatg gagtcaatgg aggccgcgct gaaagccgtt ctggcacaat taagcgccgc    6900
gcaacgcgca aatgtcgttg gcattggcgt tgacagcacc ggctctacgc cagcgccgat    6960
tgacgccgac ggtaacgtcc tggcgctgcg tccagagttc gccgagaacc cgaatgcgat    7020
gtttgtgctg tggaaagatc acaccgccgt ggaagaggcc gacgaaatca ctcgtctgtg    7080
ccataagcca ggcaag                                                    7096
```

<210> SEQ ID NO 3
<211> LENGTH: 561
<212> TYPE: PRT
<213> ORGANISM: Artificial Sequence
<220> FEATURE:
<223> OTHER INFORMATION: Signal peptide containing Crm197 amino acid
      sequence expressed from p932

<400> SEQUENCE: 3

```
Met Lys Lys Ile Trp Leu Ala Leu Ala Gly Leu Val Leu Ala Phe Ser
1               5                   10                  15

Ala Ser Ala Ala Asp Asp Val Val Asp Ser Ser Lys Ser Phe Val Met
            20                  25                  30

Glu Asn Phe Ser Ser Tyr His Gly Thr Lys Pro Gly Tyr Val Asp Ser
        35                  40                  45

Ile Gln Lys Gly Ile Gln Lys Pro Lys Ser Gly Thr Gln Gly Asn Tyr
    50                  55                  60

Asp Asp Asp Trp Lys Glu Phe Tyr Ser Thr Asp Asn Lys Tyr Asp Ala
65                  70                  75                  80

Ala Gly Tyr Ser Val Asp Asn Glu Asn Pro Leu Ser Gly Lys Ala Gly
                85                  90                  95

Gly Val Val Lys Val Thr Tyr Pro Gly Leu Thr Lys Val Leu Ala Leu
            100                 105                 110

Lys Val Asp Asn Ala Glu Thr Ile Lys Lys Glu Leu Gly Leu Ser Leu
        115                 120                 125

Thr Glu Pro Leu Met Glu Gln Val Gly Thr Glu Glu Phe Ile Lys Arg
    130                 135                 140

Phe Gly Asp Gly Ala Ser Arg Val Val Leu Ser Leu Pro Phe Ala Glu
145                 150                 155                 160

Gly Ser Ser Ser Val Glu Tyr Ile Asn Asn Trp Glu Gln Ala Lys Ala
                165                 170                 175

Leu Ser Val Glu Leu Glu Ile Asn Phe Glu Thr Arg Gly Lys Arg Gly
            180                 185                 190

Gln Asp Ala Met Tyr Glu Tyr Met Ala Gln Ala Cys Ala Gly Asn Arg
        195                 200                 205

Val Arg Arg Ser Val Gly Ser Ser Leu Ser Cys Ile Asn Leu Asp Trp
    210                 215                 220

Asp Val Ile Arg Asp Lys Thr Lys Thr Lys Ile Glu Ser Leu Lys Glu
225                 230                 235                 240

His Gly Pro Ile Lys Asn Lys Met Ser Glu Ser Pro Asn Lys Thr Val
                245                 250                 255

Ser Glu Glu Lys Ala Lys Gln Tyr Leu Glu Glu Phe His Gln Thr Ala
            260                 265                 270

Leu Glu His Pro Glu Leu Ser Glu Leu Lys Thr Val Thr Gly Thr Asn
        275                 280                 285
```

```
Pro Val Phe Ala Gly Ala Asn Tyr Ala Ala Trp Ala Val Asn Val Ala
    290                 295                 300

Gln Val Ile Asp Ser Glu Thr Ala Asp Asn Leu Glu Lys Thr Thr Ala
305                 310                 315                 320

Ala Leu Ser Ile Leu Pro Gly Ile Gly Ser Val Met Gly Ile Ala Asp
                325                 330                 335

Gly Ala Val His His Asn Thr Glu Glu Ile Val Ala Gln Ser Ile Ala
                340                 345                 350

Leu Ser Ser Leu Met Val Ala Gln Ala Ile Pro Leu Val Gly Glu Leu
        355                 360                 365

Val Asp Ile Gly Phe Ala Ala Tyr Asn Phe Val Glu Ser Ile Ile Asn
370                 375                 380

Leu Phe Gln Val Val His Asn Ser Tyr Asn Arg Pro Ala Tyr Ser Pro
385                 390                 395                 400

Gly His Lys Thr Gln Pro Phe Leu His Asp Gly Tyr Ala Val Ser Trp
                405                 410                 415

Asn Thr Val Glu Asp Ser Ile Ile Arg Thr Gly Phe Gln Gly Glu Ser
                420                 425                 430

Gly His Asp Ile Lys Ile Thr Ala Glu Asn Thr Pro Leu Pro Ile Ala
        435                 440                 445

Gly Val Leu Leu Pro Thr Ile Pro Gly Lys Leu Asp Val Asn Lys Ser
450                 455                 460

Lys Thr His Ile Ser Val Asn Gly Arg Lys Ile Arg Met Arg Cys Arg
465                 470                 475                 480

Ala Ile Asp Gly Asp Val Thr Phe Cys Arg Pro Lys Ser Pro Val Tyr
                485                 490                 495

Val Gly Asn Gly Val His Ala Asn Leu His Val Ala Phe His Arg Ser
                500                 505                 510

Ser Ser Glu Lys Ile His Ser Asn Glu Ile Ser Ser Asp Ser Ile Gly
        515                 520                 525

Val Leu Gly Tyr Gln Lys Thr Val Asp His Thr Lys Val Asn Ser Lys
530                 535                 540

Leu Ser Leu Phe Phe Glu Ile Lys Ser Gly Ser His His His His
545                 550                 555                 560

His

<210> SEQ ID NO 4
<211> LENGTH: 562
<212> TYPE: PRT
<213> ORGANISM: Artificial Sequence
<220> FEATURE:
<223> OTHER INFORMATION: Signal peptide containing Crm197 amino acid
      sequence expressed from p933

<400> SEQUENCE: 4

Met Lys Lys Ile Trp Leu Ala Leu Ala Gly Leu Val Leu Ala Phe Ser
1               5                   10                  15

Ala Met Ala Gly Ala Asp Asp Val Val Asp Ser Ser Lys Ser Phe Val
                20                  25                  30

Met Glu Asn Phe Ser Ser Tyr His Gly Thr Lys Pro Gly Tyr Val Asp
        35                  40                  45

Ser Ile Gln Lys Gly Ile Gln Lys Pro Lys Ser Gly Thr Gln Gly Asn
    50                  55                  60

Tyr Asp Asp Asp Trp Lys Glu Phe Tyr Ser Thr Asp Asn Lys Tyr Asp
65                  70                  75                  80
```

```
Ala Ala Gly Tyr Ser Val Asp Asn Glu Asn Pro Leu Ser Gly Lys Ala
             85                  90                  95
Gly Gly Val Val Lys Val Thr Tyr Pro Gly Leu Thr Lys Val Leu Ala
            100                 105                 110
Leu Lys Val Asp Asn Ala Glu Thr Ile Lys Lys Glu Leu Gly Leu Ser
            115                 120                 125
Leu Thr Glu Pro Leu Met Glu Gln Val Gly Thr Glu Phe Ile Lys
130                 135                 140
Arg Phe Gly Asp Gly Ala Ser Arg Val Val Leu Ser Leu Pro Phe Ala
145                 150                 155                 160
Glu Gly Ser Ser Val Glu Tyr Ile Asn Asn Trp Glu Gln Ala Lys
                165                 170                 175
Ala Leu Ser Val Glu Leu Glu Ile Asn Phe Glu Thr Arg Gly Lys Arg
            180                 185                 190
Gly Gln Asp Ala Met Tyr Glu Tyr Met Ala Gln Ala Cys Ala Gly Asn
            195                 200                 205
Arg Val Arg Arg Ser Val Gly Ser Ser Leu Ser Cys Ile Asn Leu Asp
            210                 215                 220
Trp Asp Val Ile Arg Asp Lys Thr Lys Thr Lys Ile Glu Ser Leu Lys
225                 230                 235                 240
Glu His Gly Pro Ile Lys Asn Lys Met Ser Glu Ser Pro Asn Lys Thr
                245                 250                 255
Val Ser Glu Glu Lys Ala Lys Gln Tyr Leu Glu Glu Phe His Gln Thr
            260                 265                 270
Ala Leu Glu His Pro Glu Leu Ser Glu Leu Lys Thr Val Thr Gly Thr
            275                 280                 285
Asn Pro Val Phe Ala Gly Ala Asn Tyr Ala Ala Trp Ala Val Asn Val
            290                 295                 300
Ala Gln Val Ile Asp Ser Glu Thr Ala Asp Asn Leu Glu Lys Thr Thr
305                 310                 315                 320
Ala Ala Leu Ser Ile Leu Pro Gly Ile Gly Ser Val Met Gly Ile Ala
                325                 330                 335
Asp Gly Ala Val His His Asn Thr Glu Glu Ile Val Ala Gln Ser Ile
            340                 345                 350
Ala Leu Ser Ser Leu Met Val Ala Gln Ala Ile Pro Leu Val Gly Glu
            355                 360                 365
Leu Val Asp Ile Gly Phe Ala Ala Tyr Asn Phe Val Glu Ser Ile Ile
            370                 375                 380
Asn Leu Phe Gln Val Val His Asn Ser Tyr Asn Arg Pro Ala Tyr Ser
385                 390                 395                 400
Pro Gly His Lys Thr Gln Pro Phe Leu His Asp Gly Tyr Ala Val Ser
                405                 410                 415
Trp Asn Thr Val Glu Asp Ser Ile Ile Arg Thr Gly Phe Gln Gly Glu
            420                 425                 430
Ser Gly His Asp Ile Lys Ile Thr Ala Glu Asn Thr Pro Leu Pro Ile
            435                 440                 445
Ala Gly Val Leu Leu Pro Thr Ile Pro Gly Lys Leu Asp Val Asn Lys
450                 455                 460
Ser Lys Thr His Ile Ser Val Asn Gly Arg Lys Ile Arg Met Arg Cys
465                 470                 475                 480
Arg Ala Ile Asp Gly Asp Val Thr Phe Cys Arg Pro Lys Ser Pro Val
                485                 490                 495
```

```
Tyr Val Gly Asn Gly Val His Ala Asn Leu His Val Ala Phe His Arg
            500                 505                 510

Ser Ser Ser Glu Lys Ile His Ser Asn Glu Ile Ser Ser Asp Ser Ile
            515                 520                 525

Gly Val Leu Gly Tyr Gln Lys Thr Val Asp His Thr Lys Val Asn Ser
            530                 535                 540

Lys Leu Ser Leu Phe Phe Glu Ile Lys Ser Gly Ser His His His His
545                 550                 555                 560

His His

<210> SEQ ID NO 5
<211> LENGTH: 561
<212> TYPE: PRT
<213> ORGANISM: Artificial Sequence
<220> FEATURE:
<223> OTHER INFORMATION: translated protein sequence of expression
      plasmid p722

<400> SEQUENCE: 5

Met Lys Lys Ile Trp Leu Ala Leu Ala Gly Leu Val Leu Ala Phe Ser
1               5                   10                  15

Ala Met Gly Ala Asp Asp Val Val Asp Ser Ser Lys Ser Phe Val Met
            20                  25                  30

Glu Asn Phe Ser Ser Tyr His Gly Thr Lys Pro Gly Tyr Val Asp Ser
        35                  40                  45

Ile Gln Lys Gly Ile Gln Lys Pro Lys Ser Gly Thr Gln Gly Asn Tyr
    50                  55                  60

Asp Asp Asp Trp Lys Glu Phe Tyr Ser Thr Asp Asn Lys Tyr Asp Ala
65                  70                  75                  80

Ala Gly Tyr Ser Val Asp Asn Glu Asn Pro Leu Ser Gly Lys Ala Gly
                85                  90                  95

Gly Val Val Lys Val Thr Tyr Pro Gly Leu Thr Lys Val Leu Ala Leu
            100                 105                 110

Lys Val Asp Asn Ala Glu Thr Ile Lys Lys Glu Leu Gly Leu Ser Leu
            115                 120                 125

Thr Glu Pro Leu Met Glu Gln Val Gly Thr Glu Phe Ile Lys Arg
        130                 135                 140

Phe Gly Asp Gly Ala Ser Arg Val Val Leu Ser Leu Pro Phe Ala Glu
145                 150                 155                 160

Gly Ser Ser Ser Val Glu Tyr Ile Asn Asn Trp Glu Gln Ala Lys Ala
                165                 170                 175

Leu Ser Val Glu Leu Glu Ile Asn Phe Glu Thr Arg Gly Lys Arg Gly
            180                 185                 190

Gln Asp Ala Met Tyr Glu Tyr Met Ala Gln Ala Cys Ala Gly Asn Arg
        195                 200                 205

Val Arg Arg Ser Val Gly Ser Ser Leu Ser Cys Ile Asn Leu Asp Trp
    210                 215                 220

Asp Val Ile Arg Asp Lys Thr Lys Thr Lys Ile Glu Ser Leu Lys Glu
225                 230                 235                 240

His Gly Pro Ile Lys Asn Lys Met Ser Glu Ser Pro Asn Lys Thr Val
                245                 250                 255

Ser Glu Glu Lys Ala Lys Gln Tyr Leu Glu Glu Phe His Gln Thr Ala
            260                 265                 270

Leu Glu His Pro Glu Leu Ser Glu Leu Lys Thr Val Thr Gly Thr Asn
        275                 280                 285
```

```
Pro Val Phe Ala Gly Ala Asn Tyr Ala Ala Trp Ala Val Asn Val Ala
        290                 295                 300

Gln Val Ile Asp Ser Glu Thr Ala Asp Asn Leu Glu Lys Thr Thr Ala
305                 310                 315                 320

Ala Leu Ser Ile Leu Pro Gly Ile Gly Ser Val Met Gly Ile Ala Asp
                325                 330                 335

Gly Ala Val His His Asn Thr Glu Glu Ile Val Ala Gln Ser Ile Ala
            340                 345                 350

Leu Ser Ser Leu Met Val Ala Gln Ala Ile Pro Leu Val Gly Glu Leu
        355                 360                 365

Val Asp Ile Gly Phe Ala Ala Tyr Asn Phe Val Glu Ser Ile Ile Asn
370                 375                 380

Leu Phe Gln Val Val His Asn Ser Tyr Asn Arg Pro Ala Tyr Ser Pro
385                 390                 395                 400

Gly His Lys Thr Gln Pro Phe Leu His Asp Gly Tyr Ala Val Ser Trp
                405                 410                 415

Asn Thr Val Glu Asp Ser Ile Ile Arg Thr Gly Phe Gln Gly Glu Ser
            420                 425                 430

Gly His Asp Ile Lys Ile Thr Ala Glu Asn Thr Pro Leu Pro Ile Ala
        435                 440                 445

Gly Val Leu Leu Pro Thr Ile Pro Gly Lys Leu Asp Val Asn Lys Ser
450                 455                 460

Lys Thr His Ile Ser Val Asn Gly Arg Lys Ile Arg Met Arg Cys Arg
465                 470                 475                 480

Ala Ile Asp Gly Asp Val Thr Phe Cys Arg Pro Lys Ser Pro Val Tyr
                485                 490                 495

Val Gly Asn Gly Val His Ala Asn Leu His Val Ala Phe His Arg Ser
            500                 505                 510

Ser Ser Glu Lys Ile His Ser Asn Glu Ile Ser Ser Asp Ser Ile Gly
        515                 520                 525

Val Leu Gly Tyr Gln Lys Thr Val Asp His Thr Lys Val Asn Ser Lys
530                 535                 540

Leu Ser Leu Phe Phe Glu Ile Lys Ser Gly Ser His His His His His
545                 550                 555                 560

His

<210> SEQ ID NO 6
<211> LENGTH: 535
<212> TYPE: PRT
<213> ORGANISM: Corynebacterium diphtheriae
<220> FEATURE:
<223> OTHER INFORMATION: secreted mature CRM197 protein

<400> SEQUENCE: 6

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
```

```
            85                  90                  95
Asp Asn Ala Glu Thr Ile Lys Lys Glu Leu Gly Leu Ser Leu Thr Glu
            100                 105             110

Pro Leu Met Glu Gln Val Gly Thr Glu Glu Phe Ile Lys Arg Phe Gly
        115             120             125

Asp Gly Ala Ser Arg Val Val Leu Ser Leu Pro Phe Ala Glu Gly Ser
        130             135             140

Ser Ser Val Glu Tyr Ile Asn Asn Trp Glu Gln Ala Lys Ala Leu Ser
145             150             155             160

Val Glu Leu Glu Ile Asn Phe Glu Thr Arg Gly Lys Arg Gly Gln Asp
                165             170             175

Ala Met Tyr Glu Tyr Met Ala Gln Ala Cys Ala Gly Asn Arg Val Arg
            180             185             190

Arg Ser Val Gly Ser Ser Leu Ser Cys Ile Asn Leu Asp Trp Asp Val
            195             200             205

Ile Arg Asp Lys Thr Lys Thr Lys Ile Glu Ser Leu Lys Glu His Gly
        210             215             220

Pro Ile Lys Asn Lys Met Ser Glu Ser Pro Asn Lys Thr Val Ser Glu
225             230             235             240

Glu Lys Ala Lys Gln Tyr Leu Glu Glu Phe His Gln Thr Ala Leu Glu
                245             250             255

His Pro Glu Leu Ser Glu Leu Lys Thr Val Thr Gly Thr Asn Pro Val
            260             265             270

Phe Ala Gly Ala Asn Tyr Ala Ala Trp Ala Val Asn Val Ala Gln Val
        275             280             285

Ile Asp Ser Glu Thr Ala Asp Asn Leu Glu Lys Thr Thr Ala Ala Leu
        290             295             300

Ser Ile Leu Pro Gly Ile Gly Ser Val Met Gly Ile Ala Asp Gly Ala
305             310             315             320

Val His His Asn Thr Glu Glu Ile Val Ala Gln Ser Ile Ala Leu Ser
                325             330             335

Ser Leu Met Val Ala Gln Ala Ile Pro Leu Val Gly Glu Leu Val Asp
            340             345             350

Ile Gly Phe Ala Ala Tyr Asn Phe Val Glu Ser Ile Ile Asn Leu Phe
        355             360             365

Gln Val Val His Asn Ser Tyr Asn Arg Pro Ala Tyr Ser Pro Gly His
        370             375             380

Lys Thr Gln Pro Phe Leu His Asp Gly Tyr Ala Val Ser Trp Asn Thr
385             390             395             400

Val Glu Asp Ser Ile Ile Arg Thr Gly Phe Gln Gly Glu Ser Gly His
                405             410             415

Asp Ile Lys Ile Thr Ala Glu Asn Thr Pro Leu Pro Ile Ala Gly Val
            420             425             430

Leu Leu Pro Thr Ile Pro Gly Lys Leu Asp Val Asn Lys Ser Lys Thr
            435             440             445

His Ile Ser Val Asn Gly Arg Lys Ile Arg Met Arg Cys Arg Ala Ile
        450             455             460

Asp Gly Asp Val Thr Phe Cys Arg Pro Lys Ser Pro Val Tyr Val Gly
465             470             475             480

Asn Gly Val His Ala Asn Leu His Val Ala Phe His Arg Ser Ser Ser
                485             490             495

Glu Lys Ile His Ser Asn Glu Ile Ser Ser Asp Ser Ile Gly Val Leu
            500             505             510
```

```
Gly Tyr Gln Lys Thr Val Asp His Thr Lys Val Asn Ser Lys Leu Ser
        515                 520                 525

Leu Phe Phe Glu Ile Lys Ser
    530                 535

<210> SEQ ID NO 7
<211> LENGTH: 4
<212> TYPE: PRT
<213> ORGANISM: Artificial Sequence
<220> FEATURE:
<223> OTHER INFORMATION: N-terminus amino acids of recombinant CRM197

<400> SEQUENCE: 7

Ala Asp Asp Val
1

<210> SEQ ID NO 8
<211> LENGTH: 4
<212> TYPE: PRT
<213> ORGANISM: Artificial Sequence
<220> FEATURE:
<223> OTHER INFORMATION: N-terminus amino acids of recombinant CRM197

<400> SEQUENCE: 8

Gly Ala Asp Asp
1

<210> SEQ ID NO 9
<211> LENGTH: 5
<212> TYPE: PRT
<213> ORGANISM: Artificial Sequence
<220> FEATURE:
<223> OTHER INFORMATION: N-terminus amino acids of recombinant CRM197

<400> SEQUENCE: 9

Gly Ala Asp Asp Val
1               5

<210> SEQ ID NO 10
<211> LENGTH: 4
<212> TYPE: PRT
<213> ORGANISM: Artificial Sequence
<220> FEATURE:
<223> OTHER INFORMATION: N-terminus amino acids of recombinant CRM197

<400> SEQUENCE: 10

Ala Gly Ala Asp
1

<210> SEQ ID NO 11
<211> LENGTH: 4
<212> TYPE: PRT
<213> ORGANISM: Artificial Sequence
<220> FEATURE:
<223> OTHER INFORMATION: N-terminus amino acids of recombinant CRM197

<400> SEQUENCE: 11

Met Gly Ala Asp
1

<210> SEQ ID NO 12
<211> LENGTH: 6
<212> TYPE: PRT
<213> ORGANISM: Artificial Sequence
<220> FEATURE:
<223> OTHER INFORMATION: N-terminus amino acids of recombinant CRM197
```

```
<400> SEQUENCE: 12

Met Gly Ala Asp Asp Val
1               5

<210> SEQ ID NO 13
<211> LENGTH: 28
<212> TYPE: PRT
<213> ORGANISM: Artificial Sequence
<220> FEATURE:
<223> OTHER INFORMATION: N-terminal amino acids of CRM197 expressed with
      DsbA signal peptide

<400> SEQUENCE: 13

Met Lys Lys Ile Trp Leu Ala Leu Ala Gly Leu Val Leu Ala Phe Ser
1               5                   10                  15

Ala Ser Ala Ala Asp Asp Val Val Asp Ser Ser Lys
            20                  25

<210> SEQ ID NO 14
<211> LENGTH: 30
<212> TYPE: PRT
<213> ORGANISM: Artificial Sequence
<220> FEATURE:
<223> OTHER INFORMATION: N-terminal amino acids of CRM197 expressed with
      PelB signal peptide

<400> SEQUENCE: 14

Met Lys Lys Ile Trp Leu Ala Leu Ala Gly Leu Val Leu Ala Phe Ser
1               5                   10                  15

Ala Met Ala Gly Ala Asp Asp Val Val Asp Ser Ser Lys Ser
            20                  25                  30

<210> SEQ ID NO 15
<211> LENGTH: 6
<212> TYPE: PRT
<213> ORGANISM: Artificial Sequence
<220> FEATURE:
<223> OTHER INFORMATION: Signal peptide cleavage site sequence with
      cleavage between aa3 and aa4

<400> SEQUENCE: 15

Ala Ser Ala Ala Asp Asp
1               5

<210> SEQ ID NO 16
<211> LENGTH: 7
<212> TYPE: PRT
<213> ORGANISM: Artificial Sequence
<220> FEATURE:
<223> OTHER INFORMATION: Signal peptide cleavage site sequence with
      cleavage between aa3 and aa4

<400> SEQUENCE: 16

Ala Met Ala Gly Ala Asp Asp
1               5

<210> SEQ ID NO 17
<211> LENGTH: 7
<212> TYPE: PRT
<213> ORGANISM: Artificial Sequence
<220> FEATURE:
<223> OTHER INFORMATION: Signal peptide cleavage site sequence with
      cleavage between aa3 and aa4

<400> SEQUENCE: 17
```

```
Ala Ser Ala Gly Ala Asp Asp
1               5

<210> SEQ ID NO 18
<211> LENGTH: 6
<212> TYPE: PRT
<213> ORGANISM: Artificial Sequence
<220> FEATURE:
<223> OTHER INFORMATION: Signal peptide cleavage site sequence with
      cleavage between aa3 and aa4

<400> SEQUENCE: 18

Ala Met Gly Ala Asp Asp
1               5

<210> SEQ ID NO 19
<211> LENGTH: 10
<212> TYPE: PRT
<213> ORGANISM: Artificial Sequence
<220> FEATURE:
<223> OTHER INFORMATION: p722 cleavage site with cleavage between aa6
      and aa7

<400> SEQUENCE: 19

Ala Phe Ser Ala Met Gly Ala Asp Asp Val
1               5                   10

<210> SEQ ID NO 20
<211> LENGTH: 10
<212> TYPE: PRT
<213> ORGANISM: Artificial Sequence
<220> FEATURE:
<223> OTHER INFORMATION: p932 cleavage site with cleavage between aa6
      and aa7

<400> SEQUENCE: 20

Ala Phe Ser Ala Ser Ala Ala Asp Asp Val
1               5                   10

<210> SEQ ID NO 21
<211> LENGTH: 11
<212> TYPE: PRT
<213> ORGANISM: Artificial Sequence
<220> FEATURE:
<223> OTHER INFORMATION: p933 cleavage site with cleavage between aa6
      and aa7

<400> SEQUENCE: 21

Ala Phe Ser Ala Met Ala Gly Ala Asp Asp Val
1               5                   10

<210> SEQ ID NO 22
<211> LENGTH: 11
<212> TYPE: PRT
<213> ORGANISM: Artificial Sequence
<220> FEATURE:
<223> OTHER INFORMATION: p936 cleavage site with cleavage between aa6
      and aa7

<400> SEQUENCE: 22

Ala Phe Ser Ala Met Ala Gly Ala Asp Asp Val
1               5                   10

<210> SEQ ID NO 23
<211> LENGTH: 11
<212> TYPE: PRT
<213> ORGANISM: Artificial Sequence
<220> FEATURE:
```

```
<223> OTHER INFORMATION: p934 cleavage site with cleavage between aa6
      and aa7

<400> SEQUENCE: 23

Ala Phe Ser Ala Ser Ala Gly Ala Asp Asp Val
1               5                   10

<210> SEQ ID NO 24
<211> LENGTH: 12
<212> TYPE: PRT
<213> ORGANISM: Artificial Sequence
<220> FEATURE:
<223> OTHER INFORMATION: p1027 cleavage site with cleavage between aa6
      and aa7

<400> SEQUENCE: 24

Ser Ala Ser Ala Leu Ala Met Gly Ala Asp Asp Val
1               5                   10

<210> SEQ ID NO 25
<211> LENGTH: 10
<212> TYPE: PRT
<213> ORGANISM: Artificial Sequence
<220> FEATURE:
<223> OTHER INFORMATION: p1029 cleavage site with cleavage between aa6
      and aa7

<400> SEQUENCE: 25

Ser Ala Ser Ala Leu Ala Ala Asp Asp Val
1               5                   10

<210> SEQ ID NO 26
<211> LENGTH: 12
<212> TYPE: PRT
<213> ORGANISM: Artificial Sequence
<220> FEATURE:
<223> OTHER INFORMATION: p1030 cleavage site with cleavage between aa6
      and aa7

<400> SEQUENCE: 26

Ala Thr Val Ala Gln Ala Met Gly Ala Asp Asp Val
1               5                   10

<210> SEQ ID NO 27
<211> LENGTH: 10
<212> TYPE: PRT
<213> ORGANISM: Artificial Sequence
<220> FEATURE:
<223> OTHER INFORMATION: p1032 cleavage site with cleavage between aa6
      and aa7

<400> SEQUENCE: 27

Ala Thr Val Ala Gln Ala Ala Asp Asp Val
1               5                   10

<210> SEQ ID NO 28
<211> LENGTH: 12
<212> TYPE: PRT
<213> ORGANISM: Artificial Sequence
<220> FEATURE:
<223> OTHER INFORMATION: p1033 cleavage site with cleavage between aa6
      and aa7

<400> SEQUENCE: 28

Ala Gln Pro Ala Met Ala Met Gly Ala Asp Asp Val
1               5                   10
```

-continued

```
<210> SEQ ID NO 29
<211> LENGTH: 11
<212> TYPE: PRT
<213> ORGANISM: Artificial Sequence
<220> FEATURE:
<223> OTHER INFORMATION: p1018 cleavage site with cleavage between aa6
      and aa7

<400> SEQUENCE: 29

Ala Gln Pro Ala Met Ala Gly Ala Asp Asp Val
1               5                   10

<210> SEQ ID NO 30
<211> LENGTH: 10
<212> TYPE: PRT
<213> ORGANISM: Artificial Sequence
<220> FEATURE:
<223> OTHER INFORMATION: p1035 cleavage site with cleavage between aa6
      and aa7

<400> SEQUENCE: 30

Ala Gln Pro Ala Met Ala Ala Asp Asp Val
1               5                   10

<210> SEQ ID NO 31
<211> LENGTH: 12
<212> TYPE: PRT
<213> ORGANISM: Artificial Sequence
<220> FEATURE:
<223> OTHER INFORMATION: p1036 cleavage site with cleavage between aa6
      and aa7

<400> SEQUENCE: 31

Ala Gln Pro Ala Met Ala Ala Gly Ala Asp Asp Val
1               5                   10

<210> SEQ ID NO 32
<211> LENGTH: 11
<212> TYPE: PRT
<213> ORGANISM: Artificial Sequence
<220> FEATURE:
<223> OTHER INFORMATION: p938 cleavage site with cleavage between aa6
      and aa7

<400> SEQUENCE: 32

Ser Val Gln Ala His Ala Gly Ala Asp Asp Val
1               5                   10

<210> SEQ ID NO 33
<211> LENGTH: 12
<212> TYPE: PRT
<213> ORGANISM: Artificial Sequence
<220> FEATURE:
<223> OTHER INFORMATION: p1039 cleavage site with cleavage between aa6
      and aa7

<400> SEQUENCE: 33

Ser Ala Thr Ala Ser Ala Met Gly Ala Asp Asp Val
1               5                   10

<210> SEQ ID NO 34
<211> LENGTH: 10
<212> TYPE: PRT
<213> ORGANISM: Artificial Sequence
<220> FEATURE:
<223> OTHER INFORMATION: p150 cleavage site with cleavage between aa6
      and aa7

<400> SEQUENCE: 34
```

-continued

```
Ala Phe Ser Ala Ser Ala Ala Glu Glu Ala
1               5                   10
```